US010111420B2

(12) United States Patent
Roberts

(10) Patent No.: US 10,111,420 B2
(45) Date of Patent: Oct. 30, 2018

(54) WETTING COMPOSITION

(75) Inventor: Raymond John Roberts, Prahran (AU)

(73) Assignee: RJ ROBERTS CONSULTING PTY LTD, Prahran, Victoria (AU)

(*) Notice: Subject to any disclaimer, the term of this patent is extended or adjusted under 35 U.S.C. 154(b) by 555 days.

(21) Appl. No.: 14/009,825

(22) PCT Filed: Apr. 2, 2012

(86) PCT No.: PCT/AU2012/000335
§ 371 (c)(1),
(2), (4) Date: Oct. 4, 2013

(87) PCT Pub. No.: WO2012/135895
PCT Pub. Date: Oct. 11, 2012

(65) Prior Publication Data
US 2014/0045693 A1 Feb. 13, 2014

(30) Foreign Application Priority Data
Apr. 5, 2011 (AU) ................. 2011901255

(51) Int. Cl.
A01N 25/02 (2006.01)
A01N 25/30 (2006.01)
C11D 1/72 (2006.01)
C11D 1/20 (2006.01)
C08K 5/05 (2006.01)
C11D 3/20 (2006.01)
C08K 5/105 (2006.01)
C08K 5/09 (2006.01)

(52) U.S. Cl.
CPC ............. A01N 25/02 (2013.01); A01N 25/30 (2013.01); C08K 5/09 (2013.01); C08K 5/105 (2013.01); C11D 1/72 (2013.01); C11D 3/2013 (2013.01)

(58) Field of Classification Search
None
See application file for complete search history.

(56) References Cited

U.S. PATENT DOCUMENTS

| 2,221,933 | A | 11/1940 | Eitelman et al. |
| 3,900,307 | A * | 8/1975 | Abramitis ................ 504/142 |
| 4,098,694 | A | 7/1978 | Perlaky |
| 4,141,871 | A | 2/1979 | Shimp et al. |
| 4,396,738 | A | 8/1983 | Powell et al. |
| 5,273,684 | A | 12/1993 | Traber et al. |
| 5,300,154 | A | 4/1994 | Ferber et al. |
| 5,620,788 | A | 4/1997 | Garavaglia et al. |
| 6,150,320 | A | 11/2000 | McDonell et al. |
| 6,652,766 | B1 * | 11/2003 | Frankenbach ........... C11D 1/62 252/8.61 |
| 7,560,494 | B2 | 7/2009 | Steinbrenner et al. |
| 2005/0049167 | A1 | 3/2005 | Noerenberg et al. |

FOREIGN PATENT DOCUMENTS

| AU | 2008249536 A1 | 6/2009 |
| DE | 19956237 A1 | 5/2001 |
| FR | 2495500 A1 | 6/1982 |
| NZ | 556299 A | 6/2009 |
| WO | 1992007058 A1 | 4/1992 |
| WO | 2006127937 A2 | 11/2006 |

OTHER PUBLICATIONS

Oxford English Dictionary definition: application accessed Nov. 16, 2016.*
Lin et al. (Langmuir 1997, 13(23) 6211-6218) (Year: 1997).*
International Search Report for PCT/AU2012/000335, dated Jun. 7, 2012.
International Preliminary Report on Patentability for PCT/AU2012/000335, dated Oct. 8, 2013.
Roberts, Raymond J. 'Solving the problem of chipout in laminated particleboard and improving the performance of high speed blenders'. Abstract of Presentation During the International Wood Composites Symposium 2011, Apr. 2011. RJRoberts Consulting Pty. Ltd.
Roberts, Raymond J. 'Blending Efficiency Part A: Solving the Problem of Chipout in Laminated Particleboard'. Abstract Presented During the International Wood Composites Symposium, 2011.
Roberts, Raymond J. 'Blending Efficiency Part B: Core Blending and How to Improve it'. Presented During the International Wood Composites Symposium, 2011.
European search opinion and supplementary European search report for European Application No. EP 12767947.0, dated Nov. 12, 2014.

* cited by examiner

Primary Examiner — Abigail Vanhorn
Assistant Examiner — Jessica M Kassa
(74) Attorney, Agent, or Firm — Brian C. Trinque; Lathrop Gage LLP

(57) ABSTRACT

The invention relates to a wetting composition comprising greater than or equal to about 50 wt % of a C5 to C12 alcohol; and a surfactant, methods for using the wetting composition and products containing the wetting composition.

17 Claims, 3 Drawing Sheets (a) (b)

(a) (b)

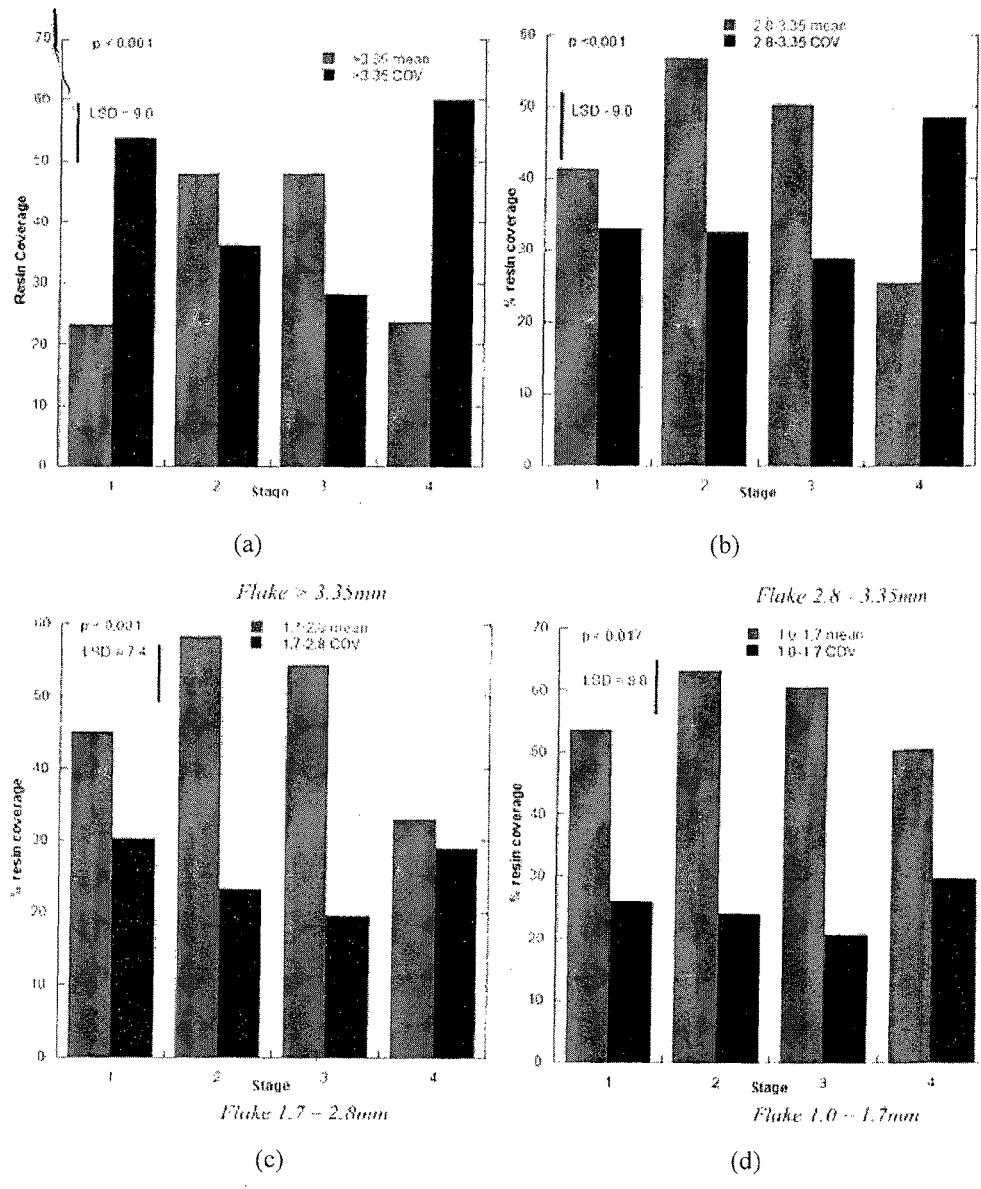
*Fig 3(a) to (d)*

*(e)*

WETTING COMPOSITION

RELATED APPLICATIONS

This application is a 35 U.S.C. § 371 filing of International Application No. PCT/AU2012/000335, filed Apr. 2, 2012, which claims priority to Australian Patent Application No. 2011901255, filed on Apr. 5, 2011. The entire contents of each of these applications are incorporated herein by reference.

FIELD OF THE INVENTION

The present invention relates to the wetting of low energy surfaces. In particular, the invention relates to a wetting composition that can be added to an aqueous liquid in order to increase the ability of the liquid to wet a low energy surface. Also disclosed are methods for increasing the aqueous wettability of a low energy surface. In some aspects, the invention relates to methods for decreasing the surface tension of an aqueous liquid by adding a wetting composition and to aqueous liquids so produced.

BACKGROUND

Wetting is the interaction of a liquid with a solid (or another liquid) and the subsequent spreading. Wetting and non-wetting are common phenomena in nature. For example, plants have self-cleaning surfaces due to an interdependence of water repellence, surface roughness and reduced particle adhesion. Industry is also full of examples where the spreading of liquids is of paramount importance. The application of water, stain or static resistant coatings is of concern in the textile industry. Adhesion of inks and protective film coatings to polymer film products used in the photographic and electronic industries are other examples. Wetting has become key in the development of many technologies and for this reason the fundamental mechanisms involved in wetting have been investigated.

The macroscopic behaviour of a liquid is defined in terms of the contact angle ($\Theta$). The contact angle is the tangent that the liquid (L)/vapour (V) interface makes with the solid (S) surface at the three phase contact line.

The contact angle is commonly used to quantify the wetting of a substrate. When a liquid drop is placed on a surface, the liquid contact angle will be in the range of 0° to 180°. An angle of 0° indicates complete wetting and the liquid forms a thin film over the surface of the substrate; for example, this type of wetting is observed on clean quartz surfaces.

Partial wetting occurs when the contact angle is finite and the liquid drop on the surface forms an equilibrium shape, defined by the laws of Laplace.

The contact angle can be defined using the principle of energy minimization as well as a force balance at the solid-liquid (SL), solid-vapour (SV) and liquid-vapour (LV) interfaces. The Young equation relates the contact angle to the surface energies of the three-phase line of contact. (Equation 1):

$$\cos\theta = \frac{\gamma_{SV} - \gamma_{SL}}{\gamma_{LV}} \quad (1)$$

Surfaces that have a low energy are not readily wet by high surface energy liquids such as aqueous liquids including water. These surfaces can therefore be said to be hydrophobic. The poor aqueous wettability of the low energy surface can pose a problem when the aqueous liquid is desirably spread on the surface for some reason. The aqueous liquid may be, for example, a carrier of an active compound that is desirably delivered to the surface. The active compound can be e.g. a drug compound, an agricultural composition or a dye. Alternatively (or in addition) the aqueous liquid could be for the purpose of forming a coating over the surface of the substrate, perhaps to modify the substrate surface.

By way of example, it is desirable for dyes such as inks to spread onto paper. Furthermore, dyes for textiles made of fibres such as nylon, wool and silk preferably wet the surfaces of the fibres in order to give an even coverage by the dye on the fibre. The wetting ability of the dye bath is particularly important when dyeing nylon fibres which have been treated with a fluorochemical which renders the surface inherently hydrophobic.

In the agricultural industry, agricultural compositions are applied to flora to deliver an active compound such as a herbicide, fungicide and pesticide. Typically, the active compound is delivered in an aqueous liquid system as a foliar spray. The components of a plant such as the leaves, shoots and stalks, however, are inherently hydrophobic which means the wettability of the target surfaces by the foliar spray must be controlled in order to ensure the active compound reaches and coats the surfaces and does not just run off to top-soil.

The wetting of particle surfaces by aqueous liquids poses problems when the particles are inherently hydrophobic and/or when the void spaces between the particles prevents penetration of the liquid into the substrate. The coating of particles can be desirable when the surface chemistry of the particle is advantageously changed, for example if the particles are required to be negatively charged or positively charged.

Methods and compositions that improve the aqueous wettability of a low energy hydrophobic surface are desirable.

The aqueous liquid that is desirably spread onto a surface can be a complex liquid such as a aqueous-based glue or resin. Articles are impregnated and/or coated with resin for many reasons including to add strength, durability and/or to improve the aesthetic of the product. If individual smaller articles are coated with a resin and those articles are combined together, the resin can function as glue since it will harden upon exposure to conditions that cause the resin to cure.

The majority of all photographs produced today are produced on resin-coated photo-paper. The paper base of resin-coated photo-papers is sealed by two polyethylene layers, making it substantially impenetrable to liquids. During the sealing process, there are no chemicals or water absorbed into the paper base, so the time needed for processing, washing and drying are significantly reduced in comparison to fibre-based papers. Resin-paper prints can be finished and dried within twenty to thirty minutes and have improved dimensional stability, and furthermore do not curl upon drying.

In the panel board industry, décor papers are impregnated and coated with resin prior to lamination onto wood based panels. Initially the décor paper is impregnated with a urea formaldehyde (UF) resin by passing the paper under tension over a pre-wetting roller. A film of resin picked up by the roller is transferred to the bottom side of the paper. The resin is given some time to penetrate into the paper before being completely immersed in a resin bath of UF to wet the top-side of the paper. The next stage of the treatment process involves coating the saturated and dried UF resin impregnated paper with a melamine formaldehyde (MF) resin. This is usually done by applying the resin onto the paper using gravure rollers. The MF resin is substantially more durable than UF resin and must contiguously cover the surface. Melamine impregnated paper is ten times more impermeable than paper treated with UF resin alone.

The aim of the first stage is to fill the void spaces (pores) of the paper with relatively inexpensive UF resin solids so, that a minimal amount of the more expensive MF resin is used in the second stage. If the paper is dipped in the UF resin bath too soon after the pre-wetting rollers, a layer of air can become trapped in the core thereby preventing the paper from being adequately saturated with UF resin. If MF resin flows into voids in the paper remaining after UF resin treatment or if the MF resin does not spread sufficiently, then insufficient MF resin may remain on the surface of the paper to effectively coat it. Defects in the resultant product may occur as a result of this mechanism because the MF resin used to treat decor paper is formulated to flow just prior to full cure in order to achieve the desired textured finish on the surface of the panel. To overcome this problem it has often been necessary to add excess MF resin to the paper to ensure there will be enough on the surface to provide a good protective coating. This is expensive and can lead to longer pressing cycles with consequential lost production and possible over-cure of the coating resin.

In the laminated particle board industry individual wood particle flakes are coated with a resin in order to ensure good coverage with the resin (glue) and therefore a strong particle board as a result. The ideal particleboard flake has a high aspect ratio i.e. a high surface to volume ratio. This enables more potential contact points to bond with other flake. The corollary to this is a dust particle which has a much lower aspect ratio, analogous to a sphere. Such particles can bond to one another at only one point, irrespective of how much resin is applied. As dry flake has a very low surface free energy i.e. is a poorly wetting surface and as the resin mix has a relatively high surface tension, the interfacial energy between the two is high. This impedes the transfer and spread of the resins on the flake surface. If large flake is not effectively resinated, it could produce zones of weakness that will impact on the integrity of the resultant panel formed from the wood particle flakes.

High speed blenders, including PAL type blenders supposedly rely on "wiping" of resin from one flake to another after resin injection. To optimise blending, operators have complex models for manipulating dwell times, involving motor current to set paddle and horn angles as well as the resistance of the out-feed flaps. However, it is still the smallest flakes that have the highest resin coverage and other larger flakes are not adequately resin wet.

Accordingly, means that improve the resin wettability of low energy surfaces such as paper and wood flakes are desirable.

WO2006/127937 describes an aqueous delivery system for low energy surface structures. The low energy surface of particular interest is PTFE. The aqueous delivery system described comprises a surfactant that is added to an aqueous liquid that will ultimately be used to wet the surface. The surfactant and the aqueous liquid together form a solution to which a wetting agent is added. The wetting agent includes alcohols and mixtures of alcohols such as hexanol and octanol. The alcohol is added incrementally to the aqueous surfactant solution (e.g. Example 6, page 13, line 34). The wetting agent and surfactant are added in amounts that ensure good emulsification of the wetting agent (page 6, lines 2 to 3). Furthermore, the surfactant is chosen to be one that is able to emulsify the desired wetting agent (page 5, lines 29 to 30). The emulsion droplets are used as the delivery means for otherwise poorly aqueous insoluble compound(s).

SUMMARY OF THE INVENTION

It has now been found that a wetting composition comprising an alcohol wetting agent and a surfactant can be prepared as an additive intended for addition to an aqueous liquid that desirably wets a low energy surface. The aqueous liquid can be a complex liquid such as a resin, for example amino formaldehyde resins, PV acetate, acrylic copolymer dispersions, resorcinol type resins and the like. The wetting composition is prepared in advance of adding the wetting composition to the aqueous liquid.

According to a first aspect of the invention there is provided a wetting composition comprising:
 greater than or equal to about 50 wt % of a C5 to C12 alcohol; and
 a surfactant.

It has also been found that the wetting composition is most efficacious if the amount of alcohol wetting agent therein is equal to or greater than about 50 wt %. The surfactant and alcohol wetting agent are present at a ratio of 1 wt %:x wt % (surfactant:alcohol) where x is 1 or greater than 1 such as 1.5, 2, 3 or 4 wt %. Advantageously, the alcohol wetting agent is present in an amount greater than about 50 wt % i.e. x is greater than 1.

The alcohol acts as a wetting agent because it lowers the surface tension of the aqueous liquid. The surfactant can also lower the surface tension of the liquid. It also can act as a deaerating agent by facilitating the release of trapped air. By providing greater than or equal to 50 wt % alcohol wetting agent, the amount of wetting agent exceeds or is at least equal to the amount of surfactant in the wetting composition. The alcohol wetting agent is thought to phase separate in the aqueous liquid in the form of small droplets and offers a large surface area for dispersion of the surfactant molecules. This is also thought to ensure that the surfactant and alcohol are present in amounts that allow for dispersal of the alcohol in the aqueous liquid to which the composition is added and does not allow for or decreases the formation of micelles. Adding the combination of alcohol and surfactant to the liquid or resin results in a quick and substantially complete wetting of the hydrophobic substances. The high level of alcohol in the wetting composition is believed to reduce the chance of formation of surfactant micelles which would interfere with the wetting action.

By "micelles do not form" or there is a "decreased formation of micelles" in the aqueous liquid, it should be understood that there may be a few micelles that self-assemble in the aqueous liquid. In some embodiments no more than about 5, 2, 1 or 0.5 vol % of micelles form in the aqueous wetting liquid.

A disadvantage of forming micelles is that there is less surfactant available for decreasing the surface tension of the aqueous liquid and for dispersing the alcohol. For example, if the surfactant forms micelles, there is less surfactant available for stabilising any emulsion that forms.

Once assembled at the interface between the alcohol and the aqueous liquid, it is thought that the surfactant is more readily able to diffuse to the three-phase contact line to thereby assist in lowering the surface tension of the aqueous liquid. In the absence of micelles, it is thought that there is a reduction in the stick-slip phenomenon as the aqueous liquid spreads across a low energy surface.

Turbidity studies of the present invention include the combined alcohol/surfactant emulsion size was so small as to be undetectable certainly to the human eye. In the pure form the surfactant is totally miscible with the alcohol and in aqueous solution the surfactant molecules attach to the surface of the alcohol in an emulsion in aqueous solution.

Once assembled at the interface between the alcohol and the aqueous liquid, it is believed, without wishing to be limited by theory, that the surfactant is more readily able to diffuse to the three-phase contact line to thereby assist in lowering the surface tension of the aqueous liquid. In the absence of micelles, it is believed that there is a reduction in the stick-slip phenomenon as the aqueous liquid spreads across a low energy surface caused by the diffusion of the surfactant molecules from within the solution to the liquid/air interphase at the three-phase contact line.

The wetting composition provides the alcohol wetting agent together with the surfactant as a combination, a concentrate or an additive. The alcohol wetting agent and surfactant are added in combination and are not added to the aqueous liquid separately. Specifically, the alcohol wetting agent is not added incrementally to an aqueous solution of the surfactant. An advantage of adding the alcohol wetting agent together with the surfactant as an additive is that the wetting composition can be sold, transported and stored conveniently before use. Another advantage is that upon addition of the wetting composition to an aqueous liquid to form a diluent, the relative concentrations of the alcohol and surfactant are fixed so the end user does not need to consider how much of each component to add to the aqueous liquid. Thus, in its broadest form the invention provides a wetting composition comprising a C5 to C12 alcohol and a surfactant.

The aqueous liquid includes water, substantially aqueous solutions and complex liquids such as aqueous-based resins or dyes. The liquid can be any aqueous liquid which desirably wets a low energy hydrophobic surface. In one embodiment, the aqueous liquid is a resin for wetting paper or wood particle flake. In another embodiment, the aqueous liquid consists of or comprises an agricultural composition.

Upon addition of the wetting composition to the aqueous liquid, the surface tension of the aqueous liquid is decreased. The surface tension of the aqueous liquid is decreased upon addition of the wetting composition compared to the surface tension of the same liquid in the absence of the wetting composition. It follows that the contact angle of the aqueous liquid having the wetting composition therein is decreased on a low energy hydrophobic surface compared to the same aqueous liquid in the absence of the wetting composition. The wetting composition when added to an aqueous liquid increases the aqueous wettability of a low energy surface. In other words, the wetting composition can be used to increase the aqueous wettability of a hydrophobic surface.

The alcohol wetting agent can comprise one or more C5 to C12 alcohols. The surfactant can comprise one or more anionic, ionic, cationic or zwitterionic surfactants.

The alcohol wetting agent may comprise one or more C5 to C12 aliphatic alcohols, preferably straight chain alcohols such as hexanol, heptanol, octanol and decanol and dodecanol, but also branched chain alcohols such as, 2-ethyl hexanol, can be used. The aliphatic alcohol should be sparingly soluble in water or insoluble and must be solubilized by the surfactant and form a stable emulsion in water.

The surfactant can comprise one or more anionic, ionic, cationic or zwitterionic surfactants.

Preferably the surfactant should be a blend of nonionic compounds that can should act as rapid wetting agents on their own, such as C6-C15 straight chain or branched aliphatic alcohol ethoxylates with a Hydrophilic Lipophilic Balance (HLB) of between 7.5-16. Ethoxylated tetra methyl decyne diols (Surfynol brands Air Industries) by themself and in admixture with aliphatic alcohol alkoxylates may be used.

Other nonionic surfactants, such as EO/PO blocked polymers are suitable with a HLB between 7.5 and 16.

Amphoteric surfactants, such as alkyl amine oxides based on C6-C12 saturated or mono unsaturated fatty acids may also be used.

Anionic surfactants such as mono or di sulphonated aliphatic straight chain or branched alcohols are preferred. Also surfactants derived from direct sulfonation of hydrocarbons, such as alpha olefine sulfonates and secondary alkane sulphonates may be used. Mono sulphonated aryl alkyl phenol like surfactants commonly known as LABS, as well as dodecyl diphenyl disulphonates (for example Dowfax 2AO) in their free acid and neutralized form may be used, especially in combination with suitable non-ionic surfactants. Dioctyl sulpho succinate and its sodium and ammonium salts (DOS) may be useful rapid wetting agents, especially in combination with aliphatic alcohol alkoxylates. Sulphonated and phosphated alkyl alcohols or alkyalkoxylates may be used.

There can be other additives in the wetting composition such as fragrance, defoamers, active compounds (e.g. drugs, agriculturally actives such as pesticides and herbicides), salts, dyes and other colourants and optionally other particles, for example, titanium dioxide, dyes, colorants, etc.

According to a second aspect of the invention, there is provided a method of lowering the surface tension of an aqueous liquid, the method comprising the step of:
  adding the wetting composition of the first aspect of the invention to the aqueous liquid.

According to a third aspect of the invention there is provided an aqueous liquid composition when prepared according to the method of the second aspect of the invention.

The aqueous liquid composition could be formed into aerosol which is a mist of liquid droplets in a gas such as air. Upon reducing the surface tension of the aqueous liquid by addition of the wetting composition of the invention, in aerosol form, the droplet size will be reduced compared to the same aqueous liquid in the absence of the wetting composition. An aerosol with reduced droplet size would provide better coverage of the aerosol spray for the same volume of applied liquid. The aerosol can be formulated for use in the paint industry, for example spray paints. Alternatively, the aerosol can be for use as a cosmetic, such as a deodoriser or a hairspray. In some embodiments, the aerosol is an agricultural spray such as an insecticide. The aerosol could also be for use as a cleaning agent.

In a fourth aspect of the present invention there is provided a method of reducing the droplet size of an aerosol spray emulsified form an aerosol spray device associated with a liquid reservoir comprising adding the wetting composition of the first aspect of the invention to the liquid reservoir associated with the aerosol spray device, and spraying the liquid from the device.

According to a fifth aspect of the invention, there is provided a method of wetting a low energy surface with a relatively high surface energy liquid, the method comprising the step of:

adding the wetting composition of the first aspect of the invention to the liquid; and contacting the low energy surface with the liquid comprising the wetting composition.

The contact angle of the liquid comprising the wetting composition is decreased on the low energy surface compared to the contact angle of the same liquid in the absence of the wetting composition.

BRIEF DESCRIPTION OF THE FIGURES

Preferred embodiments of the invention will now be described with reference to the following Figures, which are intended to be exemplary only, and in which.

DETAILED DESCRIPTION OF EMBODIMENTS OF THE INVENTION

Figure 1:
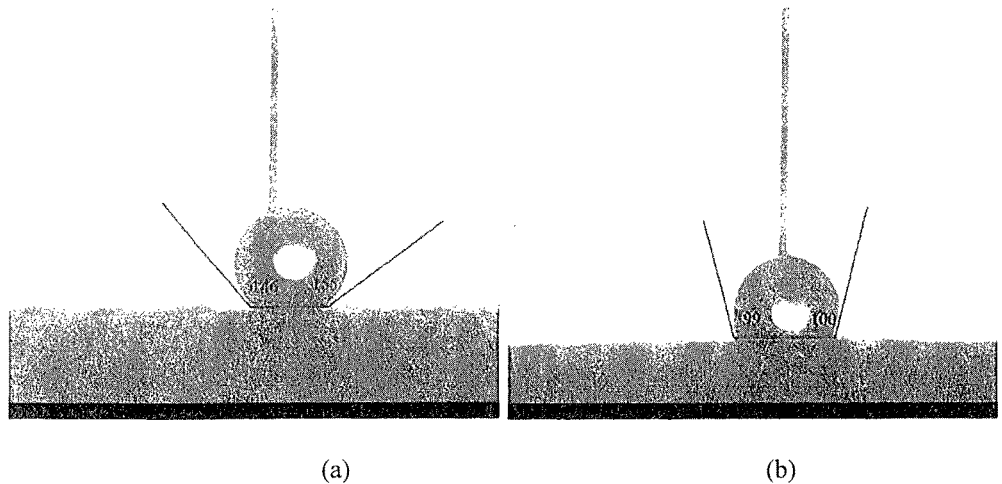
FIG. 1 (a) is a goniometry image of a resin drop on a block of slash pine; (b) is a goniometry image of a resin drop on a block of radiata pine.

The substrate that is desirably wet by the aqueous liquid comprising the wetting composition of the invention therein is not limited. The substrate can have a relatively large contiguous surface area or the substrate can be particulate. The substrate can be fibrous or porous. In one embodiment, the substrate is paper. In another embodiment, the substrate is an artificial fibre such as glass fibre insulation. The substrate can be a natural product. In one embodiment, the substrate is leather. The substrate can comprise natural fibres. The natural fibres can be wool. The natural fibres can be treated, e.g. leather treated wool. The substrate can be a seed. The substrate can be foliage including plant leaves, shoots, stalks and roots. The substrate can be wood-based or timber-based. Timber based products include wooden artefacts such as musical instruments; bamboo articles; cane and rattan; cork products and wicker products. Other timber based products include sawn timber, plywood, veneers and reconstituted wood products including chipboard, hardboard, medium and high density fibre board (MDF), orientated strand board and particle board. The substrate can also be wood particle flake that can be a component of a reconstituted wood product or can be sawn timber that is impregnated, for example pressure impregnated, or dipped with an insecticide or fungicide.

The surface of the substrate desirably wet by the aqueous liquid comprising the wetting composition has a low surface energy. The surface can have a surface energy of less than about 50, 40, 30 or 25 dynes. The surface of the substrate is hydrophobic. By "hydrophobic" it is meant that the surface has a static or advancing water contact angle of greater than about 90, 100, 110, 120, 130, 140, 150, 160, 170 or 175°. The hydrophobicity can be imparted by chemical functionality at the top few layers of the surface of the substrate. Alternatively, or in addition, the hydrophobicity is provided by surface roughness. Surface roughness includes porosity at the surface and other morphological features providing roughness.

The wetting composition can be use to increase the spreading of an aqueous liquid drop across the surface. The wetting composition can be used to increase the penetration of an aqueous liquid into a substrate. The penetration of an aqueous liquid allows for the impregnation of a porous substrate by an aqueous liquid.

The wettability of the surface can be measured by any means know to the person skilled in the art. The wettability can be determined by contact angle goniometry. Advantageously, the wettability is determined using sessile (or static) drop measurements. Alternatively, the wettability is determined using advancing and/or receding contact angle measurements optionally measured using a Wilhelmy balance. Any comparative data should use the same time of wettability measurement.

The surface of the substrate can be coated or impregnated with the aqueous liquid comprising the wetting composition. In embodiments in which the substrate surface is coated by the aqueous liquid, advantageously at least about 90, 80, 70, 60 or 50% of the total available surface area is coated. In embodiments in which a porous substrate surface is impregnated, advantageously at least about 90, 80, 70, 60 or 50% of the total available void space is filled with the liquid.

The liquid to which the wetting composition is added is aqueous or substantially aqueous. An aqueous liquid includes pure water (or substantially pure water). The liquid can consist of or comprise an agricultural composition. The agricultural composition can be for use a pesticide, insecticide, acaricide, fungicide, nematocide, disinfectant, herbicide, fertilizer or micronutrient. In one embodiment, the agricultural composition is glyphosate (N-(phosphonomethyl)glycine). Glyphosate is a broad-spectrum systemic herbicide used to kill weeds, especially annual broadleaf weeds and grasses known to compete with e.g. crops. The wetting composition of the invention could be used in a composition applied to powdered water soluble herbicides, such as Brush-off™ by Dupont.

The wetting composition can increase the ability of the agricultural composition to wet the surfaces of foliage. In another embodiment, the wetting composition can increase the ability of the agricultural composition to wet the surfaces of a timber-based substrate to provide a deterrent to pests. For example, sawn timber can be impregnated and/or dipped in an insecticide and/or fungicide before use. Furthermore, the wetting composition can improve the ability of an agricultural composition to wet seeds. For example, seeds can be coated with an insecticide and/or fungicide to protect them prior to germination. Seed coloration agents can also be added with the wetting system.

In some embodiments, the wetting composition allows the formation of a finer aerosol spray of the agricultural composition which can be applied e.g. to crops.

The liquid can consist of or comprise a pharmaceutical, neutraceutical or cosmetic. In one embodiment, the liquid consists of or comprises a drug compound. In one embodiment, the wetting composition can increase the ability of the pharmaceutical, neutraceutical or cosmetic to wet the surfaces of a human or animal body including skin, hair and/or nails. In some embodiments, the wetting composition allows the formation of a finer aerosol spray of the pharmaceutical, neutraceutical or cosmetic e.g. a hairspray. For example, a drug can be delivered as an aerosol.

An advantage of the wetting composition described is that upon addition to an aqueous liquid any solids in the liquid can be dispersed by the composition and there is thus a reduced tendency for the solids to "drop-out". This means that the wetting composition allows wetting with higher-solids-content aqueous liquids than could otherwise be used, i.e. in the absence of the wetting composition. The advantage of wetting with a high solids content liquid is that there is less chromatographic separation of the liquid upon impregnation of the liquid into a solid. A reduced separation of the liquid results in a more homogenous impregnated solid, which is ultimately stronger and more durable. Another advantage of solids dispersal is that low energy surfaces can be wet with more viscous aqueous liquids.

In some embodiments, the liquid is a complex liquid. The complex liquid can be an aqueous-based resin, a water-based paint or a dye. The resin can have a high viscosity with the ability to harden or cure. The resin can be a naturally occurring substance that is produced by certain trees. However, the resin can be natural or synthetic. The resin can be an epoxy, vinylester or polyester resin. The resin can be an amine or a formaldehyde type resin. In some embodiments, the resin is a polyvinylchloride, a polyvinyl acetate or a resorcinol resin.

The wetting composition is advantageously non-hazardous. It is also advantageous if the wetting composition is non-flammable. The wetting composition should be stable at high temperatures. In order to ensure these characteristics are met, the components of the composition must also meet these requirements individually and/or when combined together.

The surfactant, once added to the aqueous liquid, can lower the surface tension of the liquid by assembling at the liquid/vapour interface. Surfactants can act as detergents, wetting agents, emulsifiers, foaming agents and dispersants.

There can be more than one surfactant in the wetting composition and each surfactant can be the same or a different type of surfactant. When surfactant is referred to herein in the singular, it should be understood that it includes more than one surfactant within its scope unless the context makes clear otherwise.

Suitable surfactants are those that can disperse the alcohol wetting agent in the aqueous liquid to which it will be added. The dispersal can be by any means including forming an emulsion with the alcohol. Upon forming an emulsion with the alcohol there is thought to be a large amount of surfactant effectively delivered to the three-phase contact line. In forming an emulsion, there is also thought to be a decreased formation of micelles of surfactant in the aqueous liquid. This reduction in micelle formation is thought to reduce the incidence of stick-slip when wetting a surface with the aqueous liquid.

The surfactant should be at least partially and preferably totally soluble in the target aqueous liquid. By "at least partially soluble" it is meant that at least about 50, 65, 75, 80, 90 or 95% of an amount of the surfactant is capable of dissolving in the aqueous liquid. The skilled person will readily be able to determine the solubility of a chosen surfactant in an aqueous liquid solvent. Any undissolved surfactant can be removed from the solvent.

The surfactant should not undergo chemical reactions with the alcohol wetting agent in the wetting composition. Furthermore, the surfactant should be chosen not to undergo chemical reactions with the aqueous liquid to which it will be added or with any additives present in the aqueous liquid to which it will be added. There should be no chemical reactions even upon the application heat. By "not undergo chemical reaction" or "no chemical reactions" it is meant that there are no reactions that form new chemical products. There may be hydrogen bonding or other reversible chemical interactions between the chemicals. The surfactant should not chemically react with the low energy surface or adhesion problems will result. Preferably, the surfactant does not form hydrogen or other bonds with the low energy surface.

The surfactant is advantageously chosen to be non-toxic and non-flammable. The surfactant should not adversely affect the characteristics of the aqueous liquid to which it will be added, other than to reduce or assist in reducing its surface tension. It is advantageous if the surfactant does not change the aqueous liquid characteristics including colour, viscosity and odour.

Where the surfactant is for use in an agricultural composition, the surfactant should be selected to be biodegradable and non-toxic to fish and other organisms present in natural waterways. For a cosmetic or neutraceutical/pharmaceutical intended for application to the hair, skin or nails, the surfactant should be selected to be non-allergenic and should not irritate the skin.

In embodiments in which the liquid is an aqueous-based resin, the surfactant should be selected so as not affect the ability of the resin to cure and thereby harden. It is advantageous if the surfactant is able to keep the complex aqueous liquid in the dispersed phase. This is especially important when using pigment particles such as titanium dioxide in resins. When the resin is used to coat a wood particle flake used, for example, in the formation of particle board, the surfactant should be selected to one which is heat resistant during the temperatures to which the board will be exposed during the curing process. If the surfactant is not heat resistant, any break down of the surfactant at high temperature should result in non-toxic by-products that are not deleterious to the surrounding environment. When the resin is for coating paper, the surfactant should be UV stable if it is important that the paper is not discoloured by any by-products of breakdown of the surfactant molecule.

The surfactant should be capable of reducing the dynamic wettability of the aqueous liquid to which it is added (although static measurements can be used to determine this). Some surfactants are capable of reducing the static surface tension of an aqueous liquid, but the high molecular weight and resultant low molecular mobility of some surfactants means that it is not possible to lower the dynamic surface tension of an aqueous liquid; this makes them less valuable in some embodiments.

It is desirable that the surfactant is non-foaming. Anionic surfactants, such as the sodium salts of monoalkyl or dialkyl sulfosuccinates, are able effectively to reduce the surface tension of a liquid, but using them leads to the build-up of foam during many applications. Furthermore, any finished coating produced using a solution comprising the surfactant reacts sensitively to water. Accordingly, these surfactants are not useful in most embodiments.

The surfactant can be ionic, zwitterionic, non-ionic and/or cationic. The surfactant can be an ethoxylate such as a nonylphenol alkoxylate or alcohol alkoxylate, such as an ethoxylate (sold as BL8); a dodecyl sulphate; an organo-silicone super-spreader, such as Dabco® DC 193. The surfactant can one sold under the brand Teric® (any of the Teric series, although preferred are N, 12A, 9A, 13A9, 16A, 7ADN and BL series), DS 10025® or DS 10030®, Tween®, Dynol® or Surfynol®.

In some embodiments, the surfactant is nonionic. The nonionic surfactant (which includes a blend of surfactants)

advantageously has a Hydrophilic Lipophilic Balance (HLB) greater than about 6, 7, 8, 9, 10, 11, 12, 13, 14, 15, 16 or 17.

An amphoteric surfactant, such as the C8-C12 fatty acid amine oxides, may be aqdded.

The alcohol wetting agent in the wetting composition is a water insoluble alcohol. By "water insoluble" it is meant that the alcohol does not dissolve in water even with encouragement by heat and/or agitation. Alcohols that are water insoluble are those having a chain length of C5 or longer. If the chain length is lower than C5, the alcohol is flammable which is undesirable in the wetting composition. The alcohol can be linear or branched. The wetting agent of the invention can be an alcohol having a chain length of C5 up to and including C12. This includes pentanol, hexanol, heptanol, octanol and the corresponding branched chain alcohols such as 2-ethyl hexanol and 1,4-dimethyloctanol. In one embodiment the wetting agent comprises a blend of octanol and 2-ethyl hexanol. In one embodiment, the wetting agent is octanol.

There can be more than one alcohol wetting agent. When alcohol or wetting agent is referred to herein in the singular, it should be understood that there can be more than one of either present in the wetting composition.

Advantageously, the wetting composition comprises greater than or equal to about 50 wt % of a C5 to C12 alcohol wetting agent. The wetting composition can comprise about 50, 55, 60, 65, 70, 75, 80, 85, 90 or 95 wt % of the alcohol wetting agent.

The wetting composition may comprise components other than alcohol and surfactant. For example, the alcohol wetting agent can be present with other water insoluble organics such alkanes or alkenes. Furthermore, the wetting composition may comprise additives in addition to the alcohol wetting agent and the surfactant. Additives may be present in an amount of from about 30, 20, 10, 5, 2, 1, 0.5, 0.1 or 0.05 wt % of the wetting composition. Alternatively, additives may be added to the aqueous liquid at the same time as the wetting composition. In some embodiment, additives are already present in the aqueous liquid to which the wetting composition is added.

The additives may comprise one or more of fragrances, antifoam agents, antifreeze agents, dyes (or other colourants), salts, particles (including pigment particles), stabilisers, preservatives and/or buffers.

The additive in the wetting composition may be a chemical compound that has a fragrance. The additive can be a fragrance which provides a pleasant smell to the wetting composition. The fragrance can be added to provide a pleasant smell so that in its concentrated form, the wetting composition does not have a disagreeable odour. The fragrance can remove or at least mask any disagreeable odour.

Odour intensity can be expressed using an odour intensity scale, which is a verbal description of an odor sensation to which a numerical value is assigned. Odour intensity can be divided into the following categories according to intensity:

0—no odour
1—very weak (odour threshold)
2—weak
3—distinct
4—strong
5—very strong
6—intolerable Advantageously, any fragrance additive in the wetting composition reduces the odour of the wetting composition to "weak" or lower.

In one embodiment the fragrance is an essential oil. The essential oil can be a lemon or orange oil or a pine oil. The fragrance can comprise a phenolic aldehyde. The phenolic aldehyde can be vanillin or isovanillin. The fragrance can be added in concentrated form or in a solvent as a 1, 2, 5, 10 wt % solution. For example, vanillin can be added in a solvent such as ethanol (e.g. at 10 wt %).

In the absence of additives, the wetting composition consists essentially of alcohol and surfactant. Advantageously, the surfactant is present in an amount less than about 50 wt % of the wetting composition. The surfactant can be present in an amount of at least about 49, 45, 40, 35, 30, 25, 20, 10 or 5 wt %.

The wetting composition can be added to the aqueous liquid by any means. In one embodiment, the wetting composition is added to the aqueous liquid drop wise. The addition of the wetting composition can be undertaken manually or it can be controlled by a computer which programmes a delivery system. Different aqueous liquids will require different amounts of the wetting composition in order to achieve the desired decrease in contact angle. In some embodiments, the wetting composition is added incrementally (noting that the alcohol and surfactant are still added together). Following the addition of each increment, the aqueous solution can be observed with respect to its ability to wet the low energy hydrophobic surface. Once the desired wetting has been achieved, no further amount of the wetting composition need be added to the aqueous liquid. Alternatively, a known amount of the wetting composition can be added to the aqueous solution. The known amount can be based on prior experiments.

The amount of wetting compositions added to the aqueous liquid is not limited as there is no undesirable micelle formation. Therefore, unlike surfactants which reach a certain level of wettability up to the concentration that micelles form (critical micelle concentration) the wetting composition of the invention can be added up to any practical concentration to improve wetting on very difficult to wet surfaces such as Teflon or other surfaces of very low surface energy.

The amount of the wetting composition added to the aqueous liquid should ensure that the wetting composition has an advantageous affect on the wettability of the aqueous liquid with respect to the surface. The amount of wetting composition added to the aqueous liquid can be about 10, 5, 4, 3 2, 1.5, 1, 0.15, 0.05, 0.10 or 0.005 vol %. If too much wetting composition is added, this can represent unnecessary expense. If too little is added there will be no desirable effect on wetting. In some embodiments, the amount of wetting composition is added to result in an aqueous liquid having about 0.5, 0.3, 0.1 or 0.15 wt % alcohol wetting agent. The only deleterious effect caused by overdosing with wetting composition appears to be that wetting occurs too rapidly, which is rarely a problem.

Following the addition of the wetting composition to the aqueous liquid the static or advancing aqueous contact angle at the surface can be decreased to less than about 90, 80, 70, 60, 50, 40, 30, 20, 10 or 5°. In one embodiment it is desirable to decrease the advancing contact angle to less than 10°. In some embodiments, it may be desirable to decrease the static or advancing contact angle to the minimum angle possible. In other embodiments, it may only be necessary to decrease the static or advancing contact angle by a few tens or about 10, 20, 30, 40, 50, 60, 70, 80 or 90°. The desired wettability can be determined by the person skilled in the art and the corresponding amount of wetting composition required to achieve this can be added.

The increased aqueous wettability of the low energy surface can mean that the surface can be coated more quickly with a liquid comprising the wetting composition of the invention. The wetting of the low energy surface can be one, two or three orders of magnitude faster then for liquids not making use of the invention. This represents a cost and time saving. In some embodiments, less aqueous liquid is required to coat or impregnate the surfaces of a substrate again representing significant commercial benefits. The reduced amount of liquid required to provide a coating should not have any adverse effect on product quality. With respect to resin coatings, in some embodiments, less resin will be required but there will be no change in Taber abrasion resistance, scratch, stain and/or impact resistance of the final resin coated or impregnated product.

An article comprising wood particle flake coated with the resin modified according to the invention (i.e. by the addition of the wetting composition) can have improved machinability. By improved machinability it is meant that the incidence of "chip-out" i.e removal of individual non-resinated flakes or groups of flake from the surface layer of the panel that is critical for the adhesion of the laminate and the strength of the panel is reduced. This is thought to be attributed to improved resin distribution on individual flakes and a decreased variation in resin distribution between flakes. The use of the wetting composition of the invention in this embodiment allows for flexibility in the set up of blenders designed to mix the resin and flake. This can result in reduced motor current and power savings. With respect to the resin distribution, there is a potential for reduced resin usage and/or a reduction in the density and hence amount of wood used which inevitably leads to cost savings.

In other embodiments, the wetting composition allows the formation of an aerosol comprising smaller droplets than an aerosol formed by the same liquid in the absence of the wetting composition. The aerosol is a mist of liquid droplets. The wetting composition can be added prior to the aerosol formation, or at the same time as the aerosol is formed i.e. as the droplets of mist are produced.

The smaller the droplets of an aerosol the more readily the droplets disperse in air, so it follows that a finer mist can cover a larger surface area. In one embodiment, the average droplet size of an aerosol formed using the wetting composition according to the invention is about 10, 20, 30, 40, 50, 60, 70 or 80% less than the droplet size of the same liquid in the absence of the wetting composition. In one embodiment, an aerosol prepared using the wetting composition of the present invention is able to disperse into an area 10, 20, 30, 40, 50, 60, 70 or 80% larger than an aerosol of the same liquid in the absence of the wetting composition.

Embodiments of the invention will now be described with reference to the following examples which are not limiting in any way.

EXAMPLES

Example 1

Preparation of a Wetting Composition According to One Embodiment of the Invention To form the wetting composition, 1-octanol (50 wt %) was mixed with alcohol alkoxylate (BL8) (49.9 wt %) to form a miscible solution. For ease of mechanical handling, the 1-octanol was added to the alcohol alkoxylate. Vanillin 0.1 wt % (as a 10 wt % solution in EtOH) was added to the solution.

Example 2A

Analysis of Resin Coverage on Wood Flakes in the Absence of the Wetting Composition of the Present Invention Samples of blended core and surface flake were sieved into the following fractions: >5.6 mm, 2.35-5.6 mm, 1.7-2.35 mm, 1.0-1.7 mm, 0.6-1.0 mm, 0.355-0.6 mm, 0.212-0.355 mm, 0.125-0.212 mm and <0.125 mm. For fractions larger >0.6 mm samples were treated and imaged analysed individually, whereas samples <0.6 mm were investigated as groups of flake.

Data is presented on the resin coverage of different core flake fractions from various plants in Australia (over 5000 individual particles were analysed). The plants are referred to below as Plant 1*a*, 1*b*, 2*a*, 2*b*, 2*c*, 2*d* and 3. The resin coverage data is interpreted as a measure of blending efficiency; the greater the resin coverage, the greater is the blending efficiency. Results are presented in tabular format showing the mean and coefficient of variation COV (The standard deviation divided by the mean) for each core blender.

Flake was supplied to the blenders primarily from ring knife mills. It was expected that the larger fractions would have less resin; however, what was significant was the degree of variability of resination of larger core flake. As expected, the smaller fractions had the largest amount of resin and the least variation.

Table 1 shows the variability in resin coverage of the two largest fractions. Table 2 shows the means of blending efficiencies of all fractions for the core blenders. Table 3 shows COV's of all fractions for the core blenders.

TABLE 1

The variability of resin coverage with the two largest flake fractions for all core blenders

| Press | >5.6 mm min | >5.6 mm max | 2.35-5.6 mm min | 2.35-5.6 mm max |
|---|---|---|---|---|
| Plant 1a | 7.4 | 68.7 | 12.7 | 76.4 |
| Plant 1b | 6.4 | 85.6 | 11.9 | 87.1 |
| Plant 2a | 10.2 | 62.4 | 18.9 | 77.4 |
| Plant 2b | 5.8 | 64.7 | 7.6 | 70.5 |
| Plant 2c | 8.5 | 82.3 | 6.6 | 80.9 |
| Plant 2d | 1.6 | 95.1 | 1.4 | 89.2 |
| Plant 3 | 6 | 46.5 | 4.3 | 79.9 |

TABLE 2

Means of percentage of resin coverage for all core blenders as a function of flake size fraction

| | Press | | | | | | | |
|---|---|---|---|---|---|---|---|---|
| | >5.6 mm | 2.35-5.6 mm | 1.7-2.35 mm | 1.0-1.7 mm | 0.6-1.0 mm | 0.355-0.6 mm | 0.212-0.355 mm | 0.125-0.212 mm | <0.125 mm |
| Plant 1a | 26.7 | 41.7 | 46.6 | 62.0 | 65.7 | 77.6 | 74.2 | 87.8 | 96.9 |
| Plant 1b | 32.9 | 37.4 | 43.4 | 54.6 | 55.3 | 58.8 | 67.4 | 65.1 | 89.9 |
| Plant 2a | 37.7 | 44.9 | 41.6 | 45.4 | 47.0 | 59.7 | 73.4 | 85.9 | 91.2 |
| Plant 2b | 24.0 | 24.6 | 36.9 | 43.3 | 68.2 | 84.2 | 94.7 | 97.6 | 97.5 |
| Plant 2c | 34.1 | 33.3 | 34.9 | 39.9 | 48.9 | 74.8 | 91.6 | 97.1 | 97.1 |
| Plant 2d | 32.4 | 33.8 | 42.5 | 54.0 | 78.0 | 92.0 | 98.7 | 98.7 | 100 |
| Plant 3 | 20.9 | 30.0 | 37.5 | 48.5 | 62.4 | 72.1 | 77.8 | 99.0 | 99.4 |

TABLE 3

Coefficients of variation (COV) of resin coverage for all core blenders as a function of flake size fraction

| | Press | | | | | | | |
|---|---|---|---|---|---|---|---|---|
| | >5.6 mm | 2.35-5.6 mm | 1.7-2.35 mm | 1.0-1.7 mm | 0.6-1.0 mm | 0.355-0.6 mm | 0.212-0.355 mm | 0.125-0.212 mm | <0.125 mm |
| Plant 1a | 62.6 | 53.0 | 31.7 | 18.2 | 22.9 | 32.2 | 17.0 | 7.5 | 2.5 |
| Plant 1b | 70.7 | 51.1 | 46.7 | 38.3 | 21.0 | 12.2 | 19.3 | 10.7 | 10.3 |
| Plant 2a | 52.9 | 35.3 | 43.5 | 44.7 | 33.9 | 10.1 | 7.9 | 6.0 | 2.9 |
| Plant 2b | 60.2 | 76.6 | 66.9 | 48.3 | 8.9 | 6.0 | 3.1 | 2.8 | 2.4 |
| Plant 2c | 56.8 | 54.5 | 38.6 | 62.7 | 28.6 | 14.2 | 6.0 | 2.5 | 2.4 |
| Plant 2d | 69.2 | 75.6 | 56.9 | 40.5 | 9.9 | 2.6 | 1.8 | 1.9 | 1.1 |
| Plant 3 | 60.6 | 77.8 | 56.7 | 43.2 | 23.5 | 15.6 | 10.5 | 1.6 | 1.1 |

All of the core blenders produced very poor blending of the largest flake fractions. This ranged from below 5% in some cases to above 90%.

Typically, the larger flake was resinated around the edges or raised sections of the flake. Larger flake has the potential to give particleboard higher bending strength and glue bond durability. It is therefore axiomatic that if these fractions are not blended efficiently, there could be zones of weakness in the panel necessitating the need for higher densities or resin loadings.

If the interfacial energy between flake and resin is reduced, resin coverage could be improved. This could be achieved either by increasing the surface free energy of the flake by increasing flake moisture content or by reducing the surface tension of the resin mix. The former is impractical in, single daylight or continuous presses due to the excessive build-up of steam leading to possible delamination of board or a longer de-gassing stage, leaving the only option to reduce the surface tension of the resin mix using a suitable wetting composition.

Example 2B

Figure 2:
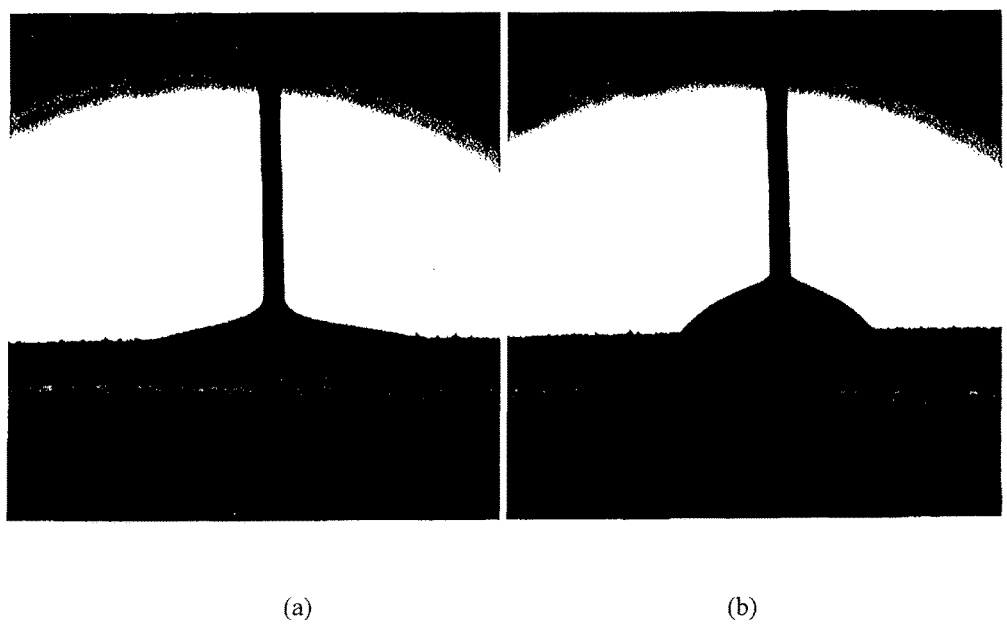
FIG. 2 (a) is a goniometry image of a resin drop, comprising the wetting composition according to one embodiment of the invention, on a block of slash pine; (b) is a goniometry image of a resin drop, comprising the wetting composition according to one embodiment of the invention, on a block of radiata pine.

Resin Wettability of Wood Flake Before and after Addition of the Wetting Composition The relative surface free energies of two sample wood particles was estimated by contact angle determination using a KSV Contact Angle Goniometer. FIG. 1 shows resin droplets on (a) slash pine and (b) radiata pine. The contact angles are (a) 150° and (b) 100°. The decrease in resin contact angle upon addition of 0.2 wt % of the wetting composition prepared in Example 1 can be seen in FIG. 2 (a) and (b).

Example 2C

Plant Trials

Two full scale plant trials were conducted on the Plant 2b line, which has PAL blenders to test under full production conditions.

Trial 1

This trial involved comparing normal blender setups without the wetting composition (Stages 1 and 4) with one treatment with the wetting composition at 0.2 wt % on wood weight with flap open and normal horn and paddle settings (Stage 2). The final treatment was Stage 3 which has the same set-up as for Stage 2, but with horn and paddle angles advanced. All settings are detailed in Table 4.

TABLE 4

Blender setups for trial 1 Plant 2b, a negative angle retards flake progress through blender and a positive angle enhances flake progression

| Blender zone | Treatment 1, 2 & 4 horn position (Normal) | Treatment 3 horn position (Advanced) |
|---|---|---|
| Inlet paddle | 10° | 10° |
| Injection zone horns 1-8 | 0° | 0° |
| Mixing zone horns 9-14 | −10 to −15° | +15° |
| Mixing zone horns 15-21 | −20° | +20 |
| Mixing zone horns 22-28 | −10 to −20° | +25° |
| Outlet zone horns 29-30 | −10 to −20° | 0° |
| Outlet zone horns 31-32 | −10° | −10° |

For the largest four flake fractions, there was a significant increase in resin distribution on flake in Stages 2 and 3 compared with Stages 1 and 4. This can be seen in FIG. 3 (*a*) to (*e*). There was no difference in resin distribution between Stages 2 and 3 which indicates that the more aggressive changes in blender setup at Stage 3 did not result in any reduction in the overall distribution of the resin on the largest flake fractions nor was there any increase in variability.

Figure 3E:
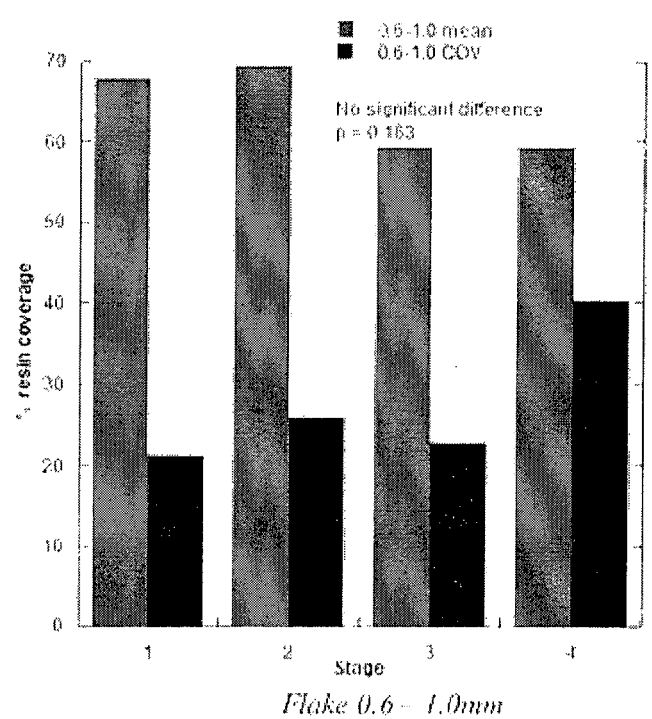
FIG. 3 shows the % resin coverage (mean and COV) of flake fractions in Stages 1 to 4, where (a) flake >3.35 mm; (b) flake 2.8-3.35 mm; (c) flake 17 mm-2.8 mm; (d) 1.0-1.7 mm; and (e) flake 0.6-1.0 mm.

FIGS. 3 (*a*) to (*e*) show reductions in variation in Stages 2 and 3 compared with Stages 1 and 4. Note also there was a significant difference in resin coverage between Stages 1 and 4 with flake from both the 2.8-3.35 mm and 1.7-2.8 mm fractions, yet these were both control Stages and show there was and still could be significant process variation that needs to be explained. There were no significant effects with the smallest fraction studied.

In the Absence of the Wetting Composition

In the flake blended without the wetting composition and with standard blender setups (Stages 1 and 4) with data pooled over the largest four flake fractions there was a very significant and substantial relationship between the length and width of the flake and resin coverage. The data was modelled as a multiple linear regression with the expression r=ax+by+c; r=resin coverage, x=flake width, y=length, c is the constant. The equation is:

$$r = (-10.8 \ast \text{width}) - (1.8 \ast \text{length}) + 78.2 (p < 0.001)$$

with the percentage of variation accounted for being over 40%. This means that 40% of the variation of resin coverage is explained by this simple linear model. In other words all other affects on resin coverage, i.e. droplet size, surface free energy of flake, surface tension of the resin, etc, are explained by the remaining 60%. Therefore, flake geometry is the most important considerations to resin distribution in a non-wetting system.

The wider the flake the more poorly it is resinated. To model it in a linear fashion is simplistic; however, it is shown that with decreasing flake length and decreasing flake width, resin coverage is greater in a non-wetting system. This is due to larger, poorly resinated flake being coated with resin around the edges, therefore it would appear that large flake in high speed blenders wets from the edge rather than along the face which. It also shows that high speed blenders cannot effectively blend larger flake. It reinforces the hypothesis that in a non-wetting system flake tends to resinate from the edge.

In the Presence of the Wetting Composition

When using the wetting composition according, the following is the relationships between flake geometry and resin coverage; the equation is:

$$r = (-2.7 \ast \text{width}) - (0.9 \ast \text{length}) + 71.9 (p < 0.001)$$

where the percentage variation accounted for being 11%, i.e. about a quarter of that when not using the wetting composition. Note the coefficients of the independent variables width and length are much lower than for the model without the wetting composition. Therefore, with the use of the wetting composition the relationship of flake geometry to resin coverage is not nearly as important. With the wetting composition, improved flake geometry can be achieved while maintaining or improving resin coverage and significantly reducing the variation in resin coverage on flake.

Trial 2

Four different dose rates of the wetting composition prepared according to Example 1 above were used: 0, 0.05, 0.1 and 0.15 wt % on dry wood weight. The wetting composition was added (dosed) volumetrically to the blender. The dosing can be undertaken as a separate step, or in conjunction with the addition of other additives to the blender. The wetting composition could be added in-line through a baffled mixing tube.

Two flake fractions were examined which comprised over 50% of the total volume of core flake: >3.35 min and 1.7-2.8 mm fractions. This equated to 960 separate samples of flake i.e. 20 from each of the fractions over 24 treatments with two flake fractions (>3.35 mm & 1.7-2.8 mm) from the core blender at Plant 2*b* (PAL blenders).

Table 5 shows the significant effect ($p<0.001$) on resin distribution with the use of the wetting composition when the data is pooled over all treatments. There is a reduction in variation in resin coverage with the use of the wetting composition (Tables 6 and 7).

TABLE 5

Resin coverage as a function of dosage of the wetting composition

| dosage (%) | 0.00 | 0.05 | 0.10 | 0.15 |
|---|---|---|---|---|
| % coverage >3.35 mm | 29.9 | 51.9 | 68.8 | 79.5 |
| % coverage 1.7-2.8 mm | 44.7 | 60.7 | 80.4 | 86.7 |

TABLE 6

Variation in resin coverage on the flake fractions >3.35 mm

| dosage (%) | COV |
|---|---|
| 0.0 | 62.9 |
| 0.05 | 32.6 |
| 0.10 | 21.7 |
| 0.15 | 16.7 |

TABLE 7

Variation in resin coverage on the flake fractions 1.7-2.8 mm

| Dosage (%) | COV |
|---|---|
| 0.0 | 41.4 |
| 0.05 | 26.2 |
| 0.10 | 12.8 |
| 0.15 | 9.9 |

Without the wetting composition, the 20 and 40 mm injection nozzle positions gave the best resin distribution results for the 1.7-2.8 mm flake fractions; however, the nozzle positions had no effect on the larger flake fraction. Without the wetting composition, the flap in the closed position gave the best resin coverage.

With the wetting composition, the nozzle position had little or no effect on resin distribution. With the use of the wetting composition at any dosage the flap being open or closed had little or no effect on the resin distribution. This means that with the wetting composition, one can operate with blender flaps open and nozzles in any position with resultant improved flake geometry and still have good resin distribution.

In regard to flake geometry, when using the wetting composition and with the flap open, there was a very significant increase in the proportion of the largest flake fraction (>3.35 mm) from 15.6% to 25.1% ($p<0.001$) and an increase in average width from 8.7 to 9.3 mm (p=0.025) i.e. greatly improving flake geometry and the potential of improving the bending strength of the particleboard along with the potential to create less fines. It would appear that opening the flap had a greater impact on flake geometry than did advancing the paddle and horn angles.

It has thus been shown that with the use of the wetting composition resin according to one embodiment of the invention, resin is more effectively and evenly distributed over larger flake than that with the modification of blending conditions alone. With the use of the wetting composition, there was a substantial improvement in flake geometry while still maintaining and improving resin distribution on the larger flake. The use of the wetting composition allows far more flexibility in the set-ups of blenders including reducing motor current and saving power.

It has been shown that variability in resin distribution is reduced with the use of the wetting composition. This gives potential for reductions in resin usage and/or reductions in density and hence amount of wood used. These could lead to significant cost savings.

Trials 3-5

Three full scale plant trials were conducted at very large particleboard plants in Europe and Asia. The purpose was to improve core blending efficiency to reduce resin loading in core flake and also separately to reduce the density of the panels by reducing the amount of blended flake used. This was achieved with no reduction in physical properties. In fact some bending modulus properties actually increased.

Materials and Methods

Similar trials were run at three plants, two of approximately 2,000 $m^3$ per day and one of approximately 1,000 $m^3$ per day. The larger plants had two PAL core blenders the first where resin was injected in the standard method with air assisted injection nozzles, and the second blender supposedly improving resin distribution. However in both cases the second blender was effectively an expensive conveyor where the horns were up to 20° advanced and the outfeed flap permanently open. In all the trials the second core blender was again set up with advanced horn settings and flap open. The smallest plant only had one PAL core blender. The two larger plants had very low quality furnish and no fresh ring mill type flake. The smallest plant had the primary source of flake from ring mill type flakers with chips from small round wood with bark on.

The trial designs were based on modifying blender setups as per Table 13 in conjunction with the addition of the wetting composition according to Tables 11 & 12. The wetting composition was 50% Octanol and 50% Teric BL8.

The trial plan was designed in such a way as to be able to draw a statistical inference, while minimising downtime in the adjustment of blender settings. As a result the design was not randomized. Analysis of variance (ANOVA) was used to analyse data. All data were checked to ensure that it complied with the assumptions of ANOVA, i.e. normality with constant variance. Statistical computation was carried out using Genstat (Lawes Agricultural Trust). The resin reduction results were analysed with density as a covariate where a linear regression was used to estimate corrections in the property data. This obviously was not required in the Density reduction (%) trials where of course density was a factor.

The design of the plant trials was according to Tables 11 & 12 however the design could be nested as there were common treatments. Therefore the trials were carried out over 4 day shifts, see Tables 14-17 where the blender setups were as follows:

| | |
|---|---|
| Day 1. | Horns normal/Flap closed |
| Day 2. | Horns normal/Flap open |
| Day 3. | Horns advanced/Flap closed |
| Day 4. | Horns advanced/Flap open |

Detailed blender horn settings are shown in Table 13.

This design resulted in only one period of downtime that being the beginning of Day 3 where the blender horns were changed. Between Days 3 & 4 the blender horns were not adjusted but the flap was kept closed. Board made in all three plants during these night shifts was adequate and saleable saving two hours downtime at the end of Day 3 and two hours at the beginning of Day 4.

The level of advancement of the horns in the mixing zones was plant specific and proprietary information. The determination of this was based on experience with different types of flake, species of flake and the size of the blender.

TABLE 11

Resin reduction treatments (density being constant)

| Blender | | Wetting composition (%) | Resin reduction (%) |
|---|---|---|---|
| N1 | Flap closed/Horns Normal | 0 | 0 |
| N2 | Flap open/Horns Normal | 0 | 0 |
| N3 | Flap closed/Horns Advanced | 0 | 0 |
| N4 | Flap open/Horns Advanced | 0 | 0 |
| R1 | Flap closed/Horns Normal | 0.2 | 0 |
| R2 | Flap closed/Horns Normal | 0.1 | 0 |
| R3 | Flap closed/Horns Normal | 0.2 | 5 |
| R4 | Flap closed/Horns Normal | 0.1 | 5 |
| R5 | Flap closed/Horns Normal | 0.2 | 10 |
| R6 | Flap closed/Horns Normal | 0.1 | 10 |
| R7 | Flap closed/Horns advanced | 0.2 | 0 |
| R8 | Flap closed/Horns advanced | 0.1 | 0 |
| R9 | Flap closed/Horns advanced | 0.2 | 5 |
| R10 | Flap closed/Horns advanced | 0.1 | 5 |
| R11 | Flap closed/Horns advanced | 0.2 | 10 |
| R12 | Flap closed/Horns advanced | 0.1 | 10 |
| R13 | Flap open/Horns advanced | 0.2 | 0 |
| R14 | Flap open/Horns advanced | 0.1 | 0 |
| R15 | Flap open/Horns advanced | 0.2 | 5 |
| R16 | Flap open/Horns advanced | 0.1 | 5 |
| R17 | Flap open/Horns advanced | 0.2 | 10 |
| R18 | Flap open/Horns advanced | 0.1 | 10 |
| R19 | Flap open/Horns normal | 0.2 | 0 |
| R20 | Flap open/Horns normal | 0.1 | 0 |
| R21 | Flap open/Horns normal | 0.2 | 5 |
| R22 | Flap open/Horns normal | 0.1 | 5 |
| R23 | Flap open/Horns normal | 0.2 | 10 |
| R24 | Flap open/Horns normal | 0.1 | 10 |

TABLE 12

Density reduction (%)treatments (resin loading being constant)

| Blender | | Wetting composition (%) | Density reduction (%) |
|---|---|---|---|
| N1 | Flap closed/Horns Normal | 0 | 0 |
| N2 | Flap open/Horns Normal | 0 | 0 |
| N3 | Flap closed/Horns Advanced | 0 | 0 |
| N4 | Flap open/Horns Advanced | 0 | 0 |
| D1 | Flap closed/Horns Normal | 0.2 | 0 |
| D2 | Flap closed/Horns Normal | 0.1 | 0 |
| D3 | Flap closed/Horns Normal | 0.2 | 5 |
| D4 | Flap closed/Horns Normal | 0.1 | 5 |
| D5 | Flap closed/Horns Normal | 0.2 | 10 |
| D6 | Flap closed/Horns Normal | 0.1 | 10 |
| D7 | Flap closed/Horns advanced | 0.2 | 0 |
| D8 | Flap closed/Horns advanced | 0.1 | 0 |

TABLE 12-continued

Density reduction (%)treatments (resin loading being constant)

| Blender | | Wetting composition (%) | Density reduction (%) |
|---|---|---|---|
| D9 | Flap closed/Horns advanced | 0.2 | 5 |
| D10 | Flap closed/Horns advanced | 0.1 | 5 |
| D11 | Flap closed/Horns advanced | 0.2 | 10 |
| D12 | Flap closed/Horns advanced | 0.1 | 10 |
| D13 | Flap open/Horns advanced | 0.2 | 0 |
| D14 | Flap open/Horns advanced | 0.1 | 0 |
| D15 | Flap open/Horns advanced | 0.2 | 5 |
| D16 | Flap open/Horns advanced | 0.1 | 5 |
| D17 | Flap open/Horns advanced | 0.2 | 10 |
| D18 | Flap open/Horns advanced | 0.1 | 10 |
| D19 | Flap open/Horns normal | 0.2 | 0 |
| D20 | Flap open/Horns normal | 0.1 | 0 |
| D21 | Flap open/Horns normal | 0.2 | 5 |
| D22 | Flap open/Horns normal | 0.1 | 5 |
| D23 | Flap open/Horns normal | 0.2 | 10 |
| D24 | Flap open/Horns normal | 0.1 | 10 |

Blender Settings

TABLE 13 paddle and horn positions
Paddle and Horn positions particleboard core blenders

| Blender zone | Horn position normal | Horn position (Advanced) |
|---|---|---|
| Inlet paddles | +40° | +40° |
| Injection zone | 0° | 0° |
| Mixing zone 1 | 0° | +10° |
| Mixing zone 2 | 0° | +10° |
| Outlet zone 1 | −10° | +10° |
| Outlet zone 2 | −10° | −10° |

TABLE 14

| | Treatments Day 1 | Resin | Density | Wetting composition % |
|---|---|---|---|---|
| Normal | | Normal | Normal | 0 |
| R1 | * Horns Normal/Flap closed | Normal | Normal | 0.2 |
| D3 | Horns Normal/Flap closed | Normal | −5% | 0.2 |
| R3 | Horns Normal/Flap closed | −5% | Normal | 0.2 |
| R5 | Horns Normal/Flap closed | −10% | Normal | 0.2 |
| D4 | Horns Normal/Flap closed | Normal | −5% | 0.1 |
| R2 | * Horns Normal/Flap closed | Normal | Normal | 0.1 |
| R4 | Horns Normal/Flap closed | −5% | Normal | 0.1 |
| R6 | Horns Normal/Flap closed | −10% | Normal | 0.1 |

TABLE 15

| | Treatments Day 2 | Resin | Density | Wetting Composition % |
|---|---|---|---|---|
| Normal | Horns normal/Flap open | Normal | Normal | 0 |
| R19 | * Horns normal/Flap open | Normal | Normal | 0.2 |
| D21 | Horns normal/Flap open | Normal | −5% | 0.2 |
| R21 | Horns normal/Flap open | −5% | Normal | 0.2 |
| R23 | Horns normal/Flap open | −10% | Normal | 0.2 |
| R20 | * Horns normal/Flap open | Normal | Normal | 0.1 |
| D22 | Horns normal/Flap open | Normal | −5% | 0.1 |
| R22 | Horns normal/Flap open | −5% | Normal | 0.1 |
| R24 | Horns normal/Flap open | −10% | Normal | 0.1 |

TABLE 16

| | Treatments Day 3 | Resin | Density | Wetting composition % |
|---|---|---|---|---|
| Normal | Horns advanced/Flap closed | Normal | Normal | 0 |
| R7 | * Horns advanced/Flap closed | Normal | Normal | 0.2 |
| D9 | Horns advanced/Flap closed | Normal | −5% | 0.2 |
| R9 | Horns advanced/Flap closed | −5% | Normal | 0.2 |
| R11 | Horns advanced/Flap closed | −10% | Normal | 0.2 |
| D10 | Horns advanced/Flap closed | Normal | −5% | 0.1 |
| R8 | * Horns advanced/Flap closed | Normal | Normal | 0.1 |
| R10 | Horns advanced/Flap closed | −5% | Normal | 0.1 |
| R12 | Horns advanced/Flap closed | −10% | Normal | 0.1 |

TABLE 17

| | Treatments Day 4 | Resin | Density | Wetting composition % |
|---|---|---|---|---|
| Normal | Horns advanced/Flap open | Normal | Normal | 0 |
| R13 | * Horns advanced/Flap open | Normal | Normal | 0.2 |
| D15 | Horns advanced/Flap open | Normal | −5% | 0.2 |
| R15 | Horns advanced/Flap open | −5% | Normal | 0.2 |
| R17 | Horns advanced/Flap open | −10% | Normal | 0.2 |
| D16 | Horns advanced/Flap open | Normal | −5% | 0.1 |
| R14 | * Horns advanced/Flap open | Normal | Normal | 0.1 |
| R16 | Horns advanced/Flap open | −5% | Normal | 0.1 |
| R18 | Horns advanced/Flap open | −10% | Normal | 0.1 |

Tables 14-17 Show treatments on a daily basis. * treatments indicate same data used for similarly numbered density trial.

Results

Results from the trial are in the form of horizontal bar charts with least significant different bars at the 95% confidence level. They show the effects of blender setup and Wetting composition (%) and either resin loading or density on IB and MOR values.

Tables 18 and 39 show a summary of the resin reduction. Where density reductions were achieved the tables they are shown in Tables 31 & 38. In both resin reduction and Density reduction (%) cases the IB values are not statistically different to "normal" values and in the case of MOR at least statistically similar or statistically better. From Table 18 and 39 all three plants were able to achieve 5 & 10% reduction in resin loadings from their current usage with the addition of Wetting composition at a (%) rate of 0.1% w/w on dry wood weight with blender horns advanced and the blender flap closed. All three plants were able to achieve 10% resin reduction with normal blender settings with both 0.1 & 0.2% Wetting composition addition. All three plants were able to achieve a 5% resin reduction with normal blender settings with 0.1% addition of Wetting composition.

In plants B & C with the recycled poor quality furnish, with the blender settings with horns advanced/Flap closed and horns normal/flap closed 5% resin savings were achieved with the addition of 0.2% Wetting composition. In plants B & C with horns normal/flap open 5% resin savings were achieved with 0.1% addition of Wetting composition.

This shows that the addition of Wetting composition gives much more flexibility in terms of blender setup while achieving resin savings with at least equal board properties.

Plant C was able to achieve 10% resin savings with the most aggressive blender setup i.e. horns advanced/flap open with both 0.1 & 0.2% addition of Wetting composition as well as a 5% reduction in resin with the same blender settings with the addition of 0.1% Wetting composition.

Note also that with Horns advanced and Flap closed it was possible at all three plants to achieve a 10% resin reduction with 0.1% Wetting composition addition however with normal blender settings it was only possible to achieve a 10% resin saving with 0.2% Wetting composition addition and a 5% reduction with 0.1% Wetting composition addition.

TABLE 18 showing treatments that resulted in successful reductions in resin loading with the use of Wetting composition and manipulation of blender settings.

| Plant | Treatment | Horn position | Flap position | Wetting composition (%) | Resin reduction (%) |
|---|---|---|---|---|---|
| A | R12 | Advanced | Closed | 0.10 | 10 |
| B | R30 | Advanced | Closed | 0.10 | 10 |
| C | R12 | Advanced | Closed | 0.10 | 10 |
| C | R11 | Advanced | Closed | 0.20 | 10 |
| A | R10 | Advanced | Closed | 0.10 | 5 |
| B | R14 | Advanced | Closed | 0.10 | 5 |
| C | R10 | Advanced | Closed | 0.10 | 5 |
| B | R6 | Advanced | Closed | 0.20 | 5 |
| C | R9 | Advanced | Closed | 0.20 | 5 |
| C | R18 | Advanced | Open | 0.10 | 10 |
| C | R17 | Advanced | Open | 0.20 | 10 |
| C | R16 | Advanced | Open | 0.10 | 5 |
| A | R6 | Normal | Closed | 0.10 | 10 |
| B | R29 | Normal | Closed | 0.10 | 10 |
| C | R6 | Normal | Closed | 0.10 | 10 |
| A | R5 | Normal | Closed | 0.20 | 10 |
| B | R5 | Normal | Closed | 0.20 | 10 |
| C | R5 | Normal | Closed | 0.20 | 10 |
| A | R4 | Normal | Closed | 0.10 | 5 |
| B | R13 | Normal | Closed | 0.10 | 5 |
| C | R4 | Normal | Closed | 0.10 | 5 |
| B | R21 | Normal | Closed | 0.20 | 5 |
| C | R3 | Normal | Closed | 0.20 | 5 |
| C | R24 | Normal | Open | 0.10 | 10 |
| A | R23 | Normal | Open | 0.20 | 10 |
| B | R16 | Normal | Open | 0.10 | 5 |
| C | R22 | Normal | Open | 0.10 | 5 |
| A | R21 | Normal | Open | 0.20 | 5 |
| B | R8 | Normal | Open | 0.20 | 5 |

TABLE 19

Effect on MOR with blender modifications, the addition of Wetting composition and reduced resin loadings on Plant A.

| Treatment | Blender | Wetting Composition (%) | Resin Reduction (%) | Density Reduction (%) | MOR (mPa) |
|---|---|---|---|---|---|
| R13 | Flap open/Horns advanced | 0.2 | 10 | 0 | 11.19 |
| R3 | Flap closed/Horns Normal | 0.2 | 5 | 0 | 11.21 |
| R11 | Flap closed/Horns advanced | 0.2 | 10 | 0 | 11.41 |
| R15 | Flap open/Horns advanced | 0.2 | 5 | 0 | 11.44 |
| R14 | Flap open/Horns advanced | 0.1 | 0 | 0 | 11.64 |
| R17 | Flap open/Horns advanced | 0.2 | 10 | 0 | 11.72 |
| R9 | Flap closed/Horns advanced | 0.2 | 5 | 0 | 11.76 |
| R22 | Flap open/Horns normal | 0.1 | 5 | 0 | 11.85 |
| R16 | Flap open/Horns advanced | 0.1 | 5 | 0 | 11.86 |
| R24 | Flap open/Horns normal | 0.1 | 10 | 0 | 12.01 |
| R7 | Flap closed/Horns advanced | 0.2 | 0 | 0 | 12.09 |
| R18 | Flap open/Horns advanced | 0.1 | 10 | 0 | 12.12 |
| R20 | Flap open/Horns normal | 0.1 | 0 | 0 | 12.14 |
| N2 | Flap closed/Horns Advanced | 0 | 0 | 0 | 12.19 |
| R10* | Flap closed/Horns advanced | 0.1 | 5 | 0 | 12.28 |
| R8* | Flap closed/Horns advanced | 0.1 | 0 | 0 | 12.35 |
| R5* | Flap closed/Horns Normal | 0.2 | 10 | 0 | 12.47 |
| R2* | Flap closed/Horns Normal | 0.1 | 0 | 0 | 12.56 |
| R4* | Flap closed/Horns Normal | 0.1 | 5 | 0 | 12.56 |
| R12* | Flap closed/Horns advanced | 0.1 | 10 | 0 | 12.68 |
| R23* | Flap open/Horns normal | 0.2 | 10 | 0 | 12.8 |
| R19* | Flap open/Horns normal | 0.2 | 0 | 0 | 12.83 |
| N1** | Flap closed/Horns Normal | 0 | 0 | 0 | 12.89 |
| N4* | Flap open/Horns Normal | 0 | 0 | 0 | 12.89 |
| R21* | Flap open/Horns normal | 0.2 | 5 | 0 | 13 |
| R6* | Flap closed/Horns Normal | 0.1 | 10 | 0 | 13.07 |
| R1* | Flap closed/Horns Normal | 0.2 | 0 | 0 | 13.18 |
| N3* | Flap open/Horns Advanced | 0 | 0 | 0 | 13.95 |

**denotes normal production.
*denotes not significantly different than normal production;
LSD = 0.6.

TABLE 20

Effect on IB with blender modifications, the addition of Wetting composition and reduced resin loadings on Plant A.

| Treatment | Blender | Wetting composition (%) | Resin reduction (%) | Density reduction (%) | IB (mPa) |
|---|---|---|---|---|---|
| R13 | Flap open/Horns advanced | 0.2 | 10 | 0 | 0.405 |
| R18 | Flap open/Horns advanced | 0.1 | 10 | 0 | 0.433 |
| R17 | Flap open/Horns advanced | 0.2 | 10 | 0 | 0.436 |
| R16 | Flap open/Horns advanced | 0.1 | 5 | 0 | 0.451 |
| R14 | Flap open/Horns advanced | 0.1 | 0 | 0 | 0.452 |
| R24 | Flap open/Horns normal | 0.1 | 10 | 0 | 0.454 |
| R20 | Flap open/Horns normal | 0.1 | 0 | 0 | 0.455 |
| R21 | Flap open/Horns normal | 0.2 | 5 | 0 | 0.467 |
| R9 | Flap closed/Horns advanced | 0.2 | 5 | 0 | 0.475 |
| R23 | Flap open/Horns normal | 0.2 | 10 | 0 | 0.479 |
| R5 | Flap closed/Horns Normal | 0.2 | 10 | 0 | 0.48 |
| R15 | Flap open/Horns advanced | 0.2 | 5 | 0 | 0.482 |
| R12 | Flap closed/Horns advanced | 0.1 | 10 | 0 | 0.492 |
| R3 | Flap closed/Horns Normal | 0.2 | 5 | 0 | 0.492 |
| R7 | Flap closed/Horns advanced | 0.2 | 0 | 0 | 0.495 |
| R22 | Flap open/Horns normal | 0.1 | 5 | 0 | 0.503 |
| R6 | Flap closed/Horns Normal | 0.1 | 10 | 0 | 0.513 |
| R11* | Flap closed/Horns advanced | 0.2 | 10 | 0 | 0.524 |
| N3* | Flap open/Horns Advanced | 0 | 0 | 0 | 0.53 |
| R19* | Flap open/Horns normal | 0.2 | 0 | 0 | 0.543 |
| R10* | Flap closed/Horns advanced | 0.1 | 5 | 0 | 0.552 |
| N2* | Flap closed/Horns Advanced | 0 | 0 | 0 | 0.554 |
| R1* | Flap closed/Horns Normal | 0.2 | 0 | 0 | 0.555 |
| R2* | Flap closed/Horns Normal | 0.1 | 0 | 0 | 0.555 |
| R4* | Flap closed/Horns Normal | 0.1 | 5 | 0 | 0.558 |
| N1** | Flap closed/Horns Normal | 0 | 0 | 0 | 0.569 |
| R8* | Flap closed/Horns advanced | 0.1 | 0 | 0 | 0.579 |
| N4* | Flap open/Horns Normal | 0 | 0 | 0 | 0.586 |

**denotes normal production.
*denotes not significantly different than normal production;
LSD = 0.045.

TABLE 21 treatments for Plant A would achieve up to a 10Resin reduction (%) while making good quality board

| Treatment | Horn position | Flap position | Wetting composition (%) | Resin reduction (%) |
|---|---|---|---|---|
| R5 | Normal | Closed | 0.2 | 10 |
| R6 | Normal | Closed | 0.1 | 10 |
| R12 | Advanced | Closed | 0.1 | 10 |
| R23 | Normal | Open | 0.2 | 10 |

TABLE 22 treatments for Plant A could achieve up to a 5Resin reduction (%) while making good quality board.

| Treatment | Horn position | Flap position | Wetting Composition (%) | Resin Reduction (%) |
|---|---|---|---|---|
| R21 | Normal | Open | 0.2 | 5 |
| R4 | Normal | Closed | 0.1 | 5 |
| R10 | Advanced | Closed | 0.1 | 5 |

TABLE 23

Effect on MOR with blender modifications, the addition of Wetting composition and reduced density on Plant A.

| Treatment | Blender | Wetting Composition (%) | Resin Reduction (%) | Density Reduction (%) | MOR (mPa) |
|---|---|---|---|---|---|
| D15 | Flap open/Horns advanced | 0.2 | 0 | 5 | 9.39 |
| D22 | Flap open/Horns normal | 0.1 | 0 | 5 | 9.9 |
| D10 | Flap closed/Horns advanced | 0.1 | 0 | 5 | 10.47 |
| D16 | Flap open/Horns advanced | 0.1 | 0 | 5 | 10.47 |
| D4 | Flap closed/Horns Normal | 0.1 | 0 | 5 | 10.6 |
| D9 | Flap closed/Horns advanced | 0.2 | 0 | 5 | 10.6 |
| D21 | Flap open/Horns normal | 0.2 | 0 | 5 | 10.66 |
| D13 | Flap open/Horns advanced | 0.2 | 0 | 10 | 11.36 |
| D3 | Flap closed/Horns Normal | 0.2 | 0 | 5 | 11.38 |
| D14 | Flap open/Horns advanced | 0.1 | 0 | 0 | 11.58 |
| D20 | Flap open/Horns normal | 0.1 | 0 | 0 | 12.18 |
| D8 | Flap closed/Horns advanced | 0.1 | 0 | 0 | 12.18 |
| D7 | Flap closed/Horns advanced | 0.2 | 0 | 0 | 12.23 |
| N2 | Flap closed/Horns Advanced | 0 | 0 | 0 | 12.49 |
| D2 | Flap closed/Horns Normal | 0.1 | 0 | 0 | 12.62 |

TABLE 23-continued

Effect on MOR with blender modifications, the addition of Wetting composition and reduced density on Plant A.

| Treatment | Blender | Wetting Composition (%) | Resin Reduction (%) | Density Reduction (%) | MOR (mPa) |
|---|---|---|---|---|---|
| N1** | Flap closed/Horns Normal | 0 | 0 | 0 | 12.81 |
| D19 | Flap open/Horns normal | 0.2 | 0 | 0 | 12.93 |
| N4 | Flap open/Horns Normal | 0 | 0 | 0 | 13.1 |
| D1 | Flap closed/Horns Normal | 0.2 | 0 | 0 | 13.13 |
| N3 | Flap open/Horns Advanced | 0 | 0 | 0 | 13.96 |

**denotes normal production,
LSD = 0.47.

TABLE 24

Effect on IB with blender modifications, the addition of Wetting composition and reduced density on Plant A.

| Treatment | Blender | Wetting composition (%) | Resin reduction (%) | Density reduction (%) | MOR (mPa) |
|---|---|---|---|---|---|
| D15 | Flap open/Horns advanced | 0.2 | 0 | 5 | 0.378 |
| D22 | Flap open/Horns normal | 0.1 | 0 | 5 | 0.39 |
| D16 | Flap open/Horns advanced | 0.1 | 0 | 5 | 0.403 |
| D21 | Flap open/Horns normal | 0.2 | 0 | 5 | 0.403 |
| D13 | Flap open/Horns advanced | 0.2 | 0 | 10 | 0.41 |
| D14 | Flap open/Horns advanced | 0.1 | 0 | 0 | 0.45 |
| D9 | Flap closed/Horns advanced | 0.2 | 0 | 5 | 0.457 |
| D20 | Flap open/Horns normal | 0.1 | 0 | 0 | 0.46 |
| D3 | Flap closed/Horns Normal | 0.2 | 0 | 5 | 0.467 |
| D4 | Flap closed/Horns Normal | 0.1 | 0 | 5 | 0.487 |
| D10 | Flap closed/Horns advanced | 0.1 | 0 | 5 | 0.5 |
| D7 | Flap closed/Horns advanced | 0.2 | 0 | 0 | 0.5 |
| N3 | Flap open/Horns Advanced | 0 | 0 | 0 | 0.503 |
| N4* | Flap open/Horns Normal | 0 | 0 | 0 | 0.53 |
| D19* | Flap open/Horns normal | 0.2 | 0 | 0 | 0.547 |
| D1* | Flap closed/Horns Normal | 0.2 | 0 | 0 | 0.553 |
| D2* | Flap closed/Horns Normal | 0.1 | 0 | 0 | 0.557 |
| N2* | Flap closed/Horns Advanced | 0 | 0 | 0 | 0.563 |
| N1** | Flap closed/Horns Normal | 0 | 0 | 0 | 0.567 |
| D8* | Flap closed/Horns advanced | 0.1 | 0 | 0 | 0.573 |

**denotes normal production,
*denotes not significantly different than normal production;
LSD = 0.05.

There was no opportunity in plant A to reduce density, the original density being below 650 kgs/m$^3$.

TABLE 25

Effect on MOR with blender modifications, the addition of Wetting composition and reduced resin loading on Plant B.

| Treatment | Blender | Wetting Composition (%) | Resin Reduction (%) | Density Reduction (%) | MOR (mPa) |
|---|---|---|---|---|---|
| R10 | Flap closed/Horns advanced | 0.1 | 5 | 0 | 10.8 |
| R12* | Flap closed/Horns advanced | 0.1 | 10 | 0 | 11.48 |
| R13* | Flap open/Horns advanced | 0.2 | 0 | 0 | 11.72 |
| R11* | Flap closed/Horns advanced | 0.2 | 10 | 0 | 11.79 |
| R6* | Flap closed/Horns Normal | 0.1 | 10 | 0 | 11.79 |
| N1** | Flap closed/Horns Normal | 0 | 0 | 0 | 12.01 |
| R7* | Flap closed/Horns advanced | 0.2 | 0 | 0 | 12.01 |
| R8* | Flap closed/Horns advanced | 0.1 | 0 | 0 | 12.03 |
| R4* | Flap closed/Horns Normal | 0.1 | 5 | 0 | 12.15 |
| R3* | Flap closed/Horns Normal | 0.2 | 5 | 0 | 12.18 |
| R2* | Flap closed/Horns Normal | 0.1 | 0 | 0 | 12.29 |
| R20* | Flap open/Horns normal | 0.1 | 0 | 0 | 12.31 |
| R9* | Flap closed/Horns advanced | 0.2 | 5 | 0 | 12.71 |
| R21* | Flap open/Horns normal | 0.2 | 5 | 0 | 12.92 |
| R24* | Flap open/Horns normal | 0.1 | 10 | 0 | 12.94 |
| R5* | Flap closed/Horns Normal | 0.2 | 10 | 0 | 12.94 |

TABLE 25-continued

Effect on MOR with blender modifications, the addition of Wetting composition and reduced resin loading on Plant B.

| Treatment | Blender | Wetting Composition (%) | Resin Reduction (%) | Density Reduction (%) | MOR (mPa) |
|---|---|---|---|---|---|
| R23*** | Flap open/Horns normal | 0.2 | 10 | 0 | 13.34 |
| R19*** | Flap open/Horns normal | 0.2 | 0 | 0 | 13.4 |
| R22*** | Flap open/Horns normal | 0.1 | 5 | 0 | 13.44 |
| R1*** | Flap closed/Horns Normal | 0.2 | 0 | 0 | 13.72 |

**denotes normal production,
*denotes not significantly different than normal production;
***denotes significantly higher values than normal production.
LSD = 0.96.

TABLE 26

Effect on IB with blender modifications, the addition of Welting composition and reduced resin loading on Plant B.

| Treatment | Blender | Wetting Composition (%) | Resin Reduction (%) | Density Reduction (%) | IB (mPa) |
|---|---|---|---|---|---|
| R13 | Flap open/Horns advanced | 0.2 | 0 | 0 | 0.347 |
| R24 | Flap open/Horns normal | 0.1 | 10 | 0 | 0.37 |
| R11 | Flap closed/Horns advanced | 0.2 | 10 | 0 | 0.376 |
| R23 | Flap open/Horns normal | 0.2 | 10 | 0 | 0.378 |
| R6 | Flap closed/Horns Normal | 0.1 | 10 | 0 | 0.399 |
| R12 | Flap closed/Horns advanced | 0.1 | 10 | 0 | 0.4 |
| R9 | Flap closed/Horns advanced | 0.2 | 5 | 0 | 0.405 |
| R21 | Flap open/Horns normal | 0.2 | 5 | 0 | 0.408 |
| R19 | Flap open/Horns normal | 0.2 | 0 | 0 | 0.413 |
| R22 | Flap open/Horns normal | 0.1 | 5 | 0 | 0.419 |
| R8 | Flap closed/Horns advanced | 0.1 | 0 | 0 | 0.42 |
| R10 | Flap closed/Horns advanced | 0.1 | 5 | 0 | 0.421 |
| R3 | Flap closed/Horns Normal | 0.2 | 5 | 0 | 0.424 |
| R20 | Flap open/Horns normal | 0.1 | 0 | 0 | 0.437 |
| R4 | Flap closed/Horns Normal | 0.1 | 5 | 0 | 0.448 |
| R7 | Flap closed/Horns advanced | 0.2 | 0 | 0 | 0.452 |
| R5 | Flap closed/Horns Normal | 0.2 | 10 | 0 | 0.472 |
| R1 | Flap closed/Horns Normal | 0.2 | 0 | 0 | 0.481 |
| R2 | Flap closed/Horns Normal | 0.1 | 0 | 0 | 0.487 |
| N1** | Flap closed/Horns Normal | 0 | 0 | 0 | 0.557 |

**denotes normal production.

TABLE 27 treatments for Plant B give adequate IB and MOR values with 10Resin reduction (%).

| Treatment | Horn position | Flap position | Wetting Composition (%) | Resin Reduction (%) |
|---|---|---|---|---|
| R5 | Normal | Closed | 0.2 | 10 |
| R30 | Advanced | Closed | 0.1 | 10 |
| R29 | Normal | Closed | 0.1 | 10 |

TABLE 28 treatments for Plant B gave adequate MOR and IB values with 5Resin reduction (%).

| Treatment | Horn position | Flap position | Wetting Composition (%) | Resin Reduction (%) |
|---|---|---|---|---|
| R13 | Normal | Closed | 0.1 | 5 |
| R21 | Normal | Closed | 0.2 | 5 |
| R14 | Advanced | Closed | 0.1 | 5 |
| R16 | Normal | Open | 0.1 | 5 |
| R8 | Normal | Open | 0.2 | 5 |
| R6 | Advanced | Closed | 0.2 | 5 |

TABLE 29

Effect on MOR with blender modifications, the addition of Wetting composition and reduced density on Plant B.

| Treatment | Blender | Wetting Composition (%) | Resin reduction (%) | Density reduction (%) | MOR (mPa) |
|---|---|---|---|---|---|
| D10 | Flap closed/Horns advanced | 0.1 | 0 | 5 | 11.04 |
| D6* | Flap closed/Horns Normal | 0.1 | 0 | 10 | 11.44 |
| D5* | Flap closed/Horns Normal | 0.2 | 0 | 10 | 11.6 |
| D4* | Flap closed/Horns Normal | 0.1 | 0 | 5 | 11.65 |
| D11* | Flap closed/Horns advanced | 0.2 | 0 | 0 | 11.7 |
| D9* | Flap closed/Horns advanced | 0.2 | 0 | 5 | 11.83 |
| D7* | Flap closed/Horns advanced | 0.2 | 0 | 0 | 12 |
| N1** | Flap closed/Horns Normal | 0 | 0 | 0 | 12.03 |
| D8* | Flap closed/Horns advanced | 0.1 | 0 | 0 | 12.04 |
| D2* | Flap closed/Horns Normal | 0.1 | 0 | 0 | 12.29 |
| D3* | Flap closed/Horns Normal | 0.2 | 0 | 5 | 12.32 |
| D20* | Flap open/Horns normal | 0.1 | 0 | 0 | 12.333 |
| D21* | Flap open/Horns normal | 0.2 | 0 | 5 | 12.46 |
| D22* | Flap open/Horns normal | 0.1 | 0 | 5 | 12.6 |
| D19*** | Flap open/Horns normal | 0.2 | 0 | 0 | 13.4 |
| D1*** | Flap closed/Horns Normal | 0.2 | 0 | 0 | 13.71 |

**denotes normal production,
*denotes not significantly different than normal production;
***denotes significantly higher values than normal production.
LSD = 0.84.

TABLE 30

Effect on MOR with blender modifications, the addition of Wetting composition and reduced density on Plant B.

| Treatment | Blender | Wetting Composition (%) | Resin Reduction (%) | Density Reduction (%) | IB (mPa) |
|---|---|---|---|---|---|
| D13 | Flap open/Horns advanced | 0.2 | 0 | 0 | 0.343 |
| D21 | Flap open/Horns normal | 0.2 | 0 | 5 | 0.39 |
| D10 | Flap closed/Horns advanced | 0.1 | 0 | 5 | 0.397 |
| D19 | Flap open/Horns normal | 0.2 | 0 | 0 | 0.413 |
| D8 | Flap closed/Horns advanced | 0.1 | 0 | 0 | 0.423 |
| D9 | Flap closed/Horns advanced | 0.2 | 0 | 5 | 0.43 |
| D6 | Flap closed/Horns Normal | 0.1 | 0 | 10 | 0.437 |
| D20 | Flap open/Horns normal | 0.1 | 0 | 0 | 0.44 |
| D22 | Flap open/Horns normal | 0.1 | 0 | 5 | 0.443 |
| D5 | Flap closed/Horns Normal | 0.2 | 0 | 10 | 0.447 |
| D3 | Flap closed/Horns Normal | 0.2 | 0 | 5 | 0.453 |
| D11 | Flap closed/Horns advanced | 0.2 | 0 | 0 | 0.457 |
| D4 | Flap closed/Horns Normal | 0.1 | 0 | 5 | 0.473 |
| D1 | Flap closed/Horns Normal | 0.2 | 0 | 0 | 0.48 |
| D2 | Flap closed/Horns Normal | 0.1 | 0 | 0 | 0.487 |
| N1** | Flap closed/Horns Normal | 0 | 0 | 0 | 0.56 |

**denotes normal production,
*denotes not significantly different than normal production;
***denotes significantly higher values than normal production.
LSD = 0.025.

TABLE 31 treatments for Plant B gave density reductions with adequate IB and MOR values.

| Treatment | Horn position | Flap position | Wetting Composition (%) | Density Reduction (%) |
|---|---|---|---|---|
| D13 | Normal | Closed | 0.2 | 5 |
| D5 | Normal | Closed | 0.2 | 5 |
| D21 | Normal | Closed | 0.2 | 10 |

TABLE 32

Effect on MOR with blender modifications, the addition of
Wetting composition and reduced resin loading on Plant C.

| Treatment | Blender | Wetting Composition (%) | Resin Reduction (%) | Density Reduction (%) | MOR (mPa) |
|---|---|---|---|---|---|
| R1* | Flap closed/Horns Normal | 0.2 | 0 | 0 | 9.326 |
| R5* | Flap closed/Horns Normal | 0.2 | 10 | 0 | 9.667 |
| N3* | Flap open/Horns Advanced | 0 | 0 | 0 | 9.792 |
| R9* | Flap closed/Horns advanced | 0.2 | 5 | 0 | 9.834 |
| R6* | Flap closed/Horns Normal | 0.1 | 10 | 0 | 9.912 |
| R23* | Flap open/Horns normal | 0.2 | 10 | 0 | 9.949 |
| R3* | Flap closed/Horns Normal | 0.2 | 5 | 0 | 10.006 |
| R21* | Flap open/Horns normal | 0.2 | 5 | 0 | 10.036 |
| R4* | Flap closed/Horns Normal | 0.1 | 5 | 0 | 10.099 |
| N1** | Flap closed/Horns Normal | 0 | 0 | 0 | 10.143 |
| R15* | Flap open/Horns advanced | 0.2 | 5 | 0 | 10.214 |
| R12* | Flap closed/Horns advanced | 0.1 | 10 | 0 | 10.259 |
| R11* | Flap closed/Horns advanced | 0.2 | 10 | 0 | 10.296 |
| R19* | Flap open/Horns normal | 0.2 | 0 | 0 | 10.308 |
| R18* | Flap open/Horns advanced | 0.1 | 10 | 0 | 10.359 |
| R17* | Flap open/Horns advanced | 0.2 | 10 | 0 | 10.393 |
| R2* | Flap closed/Horns Normal | 0.1 | 0 | 0 | 10.411 |
| R24* | Flap open/Horns normal | 0.1 | 10 | 0 | 10.604 |
| R22* | Flap open/Horns normal | 0.1 | 5 | 0 | 10.629 |
| R14* | Flap open/Horns advanced | 0.1 | 0 | 0 | 10.657 |
| R20* | Flap open/Horns normal | 0.1 | 0 | 0 | 10.736 |
| R8*** | Flap closed/Horns advanced | 0.1 | 0 | 0 | 10.783 |
| R13*** | Flap open/Horns advanced | 0.2 | 0 | 0 | 10.818 |
| R10*** | Flap closed/Horns advanced | 0.1 | 5 | 0 | 10.878 |
| R16*** | Flap open/Horns advanced | 0.1 | 5 | 0 | 10.984 |
| N2*** | Flap closed/Horns Advanced | 0 | 0 | 0 | 11.146 |
| R7*** | Flap closed/Horns advanced | 0.2 | 0 | 0 | 11.17 |
| N4*** | Flap open/Horns Normal | 0 | 0 | 0 | 11.724 |

**denotes normal production,
*denotes not significantly different than normal production;
***denotes significantly higher values than normal production.
LSD = 0.6.

TABLE 33

Effect on IB with blender modifications, the addition of
Wetting composition and reduced resin loading on Plant C.

| Treatment | Blender | Wetting composition (%) | Resin Reduction (%) | Density Reduction (%) | IB (mPa) |
|---|---|---|---|---|---|
| R21 | Flap open/Horns normal | 0.2 | 5 | 0 | 0.3364 |
| R23 | Flap open/Horns normal | 0.2 | 10 | 0 | 0.3394 |
| R15 | Flap open/Horns advanced | 0.2 | 5 | 0 | 0.3521 |
| R19 | Flap open/Horns normal | 0.2 | 0 | 0 | 0.3526 |
| N3* | Flap open/Horns Advanced | 0 | 0 | 0 | 0.3712 |
| R1* | Flap closed/Horns Normal | 0.2 | 0 | 0 | 0.3745 |
| R24* | Flap open/Horns normal | 0.1 | 10 | 0 | 0.3803 |
| R12* | Flap closed/Horns advanced | 0.1 | 10 | 0 | 0.3846 |
| R7* | Flap closed/Horns advanced | 0.2 | 0 | 0 | 0.4 |
| R18* | Flap open/Horns advanced | 0.1 | 10 | 0 | 0.4046 |
| R9* | Flap closed/Horns advanced | 0.2 | 5 | 0 | 0.4053 |
| R10* | Flap closed/Horns advanced | 0.1 | 5 | 0 | 0.4105 |
| R20* | Flap open/Horns normal | 0.1 | 0 | 0 | 0.4164 |
| R6* | Flap closed/Horns Normal | 0.1 | 10 | 0 | 0.4177 |
| R22* | Flap open/Horns normal | 0.1 | 5 | 0 | 0.4196 |
| N1** | Flap closed/Horns Normal | 0 | 0 | 0 | 0.4433 |
| R17* | Flap open/Horns advanced | 0.2 | 10 | 0 | 0.448 |
| R5* | Flap closed/Horns Normal | 0.2 | 10 | 0 | 0.4515 |
| R2* | Flap closed/Horns Normal | 0.1 | 0 | 0 | 0.4538 |
| R11* | Flap closed/Horns advanced | 0.2 | 10 | 0 | 0.4564 |
| R4* | Flap closed/Horns Normal | 0.1 | 5 | 0 | 0.4614 |
| R3* | Flap closed/Horns Normal | 0.2 | 5 | 0 | 0.4748 |
| R16* | Flap open/Horns advanced | 0.1 | 5 | 0 | 0.4834 |
| R13* | Flap open/Horns advanced | 0.2 | 0 | 0 | 0.4839 |
| N2* | Flap closed/Horns Advanced | 0 | 0 | 0 | 0.4977 |
| R14* | Flap open/Horns advanced | 0.1 | 0 | 0 | 0.5 |

TABLE 33-continued

Effect on IB with blender modifications, the addition of Wetting composition and reduced resin loading on Plant C.

| Treatment | Blender | Wetting composition (%) | Resin Reduction (%) | Density Reduction (%) | IB (mPa) |
|---|---|---|---|---|---|
| R8*** | Flap closed/Horns advanced | 0.1 | 0 | 0 | 0.52 |
| N4** | Flap open/Horns Normal | 0 | 0 | 0 | 0.5302 |

**denotes normal production,
*denotes not significantly different than normal production;
***denotes significantly higher values than normal production.
LSD = 0.067.

TABLE 34 treatments for Plant C achieve 10 resin reductions and achieve acceptable IB and MOR values in that they are not significantly different than Normal Production.

| Treatment | Horn position | Flap position | Wetting Composition (%) | Resin Reduction (%) |
|---|---|---|---|---|
| R5 | Normal | Closed | 0.2 | 10 |
| R6 | Normal | Closed | 0.1 | 10 |
| R11 | Advanced | Closed | 0.2 | 10 |
| R12 | Advanced | Closed | 0.1 | 10 |
| R17 | Advanced | Open | 0.2 | 10 |
| R18 | Advanced | Open | 0.1 | 10 |
| R24 | Normal | Open | 0.1 | 10 |

TABLE 35 treatments for Plant C achieve 5% resin reductions and achieve acceptable IB and MOR values in that they are not significantly different than Normal production

| Treatment | Horn position | Flap position | Wetting Composition (%) | Resin Reduction (%) |
|---|---|---|---|---|
| R3 | Normal | Closed | 0.2 | 5 |
| R4 | Normal | Closed | 0.1 | 5 |
| R9 | Advanced | Closed | 0.2 | 5 |
| R10 | Advanced | Closed | 0.1 | 5 |
| R16 | Advanced | Open | 0.1 | 5 |
| R22 | Normal | Open | 0.1 | 5 |

TABLE 36

Effect on IMOR with blender modifications, the addition of Wetting composition and desnity on Plant C.

| Treatment | Blender | Wetting Composition (%) | Resin Reduction (%) | Density Reduction (%) | MOR (mPa) |
|---|---|---|---|---|---|
| D11 | Flap closed/Horns advanced | 0.2 | 0 | 10 | 6.733 |
| D5 | Flap closed/Horns Normal | 0.2 | 0 | 10 | 7.067 |
| D17 | Flap open/Horns advanced | 0.2 | 0 | 10 | 7.2 |
| D12 | Flap closed/Horns advanced | 0.1 | 0 | 10 | 7.367 |
| D23 | Flap open/Horns normal | 0.2 | 0 | 10 | 7.7 |
| D24 | Flap open/Horns normal | 0.1 | 0 | 10 | 7.7 |
| D3 | Flap closed/Horns Normal | 0.2 | 0 | 5 | 8.233 |
| D6 | Flap closed/Horns Normal | 0.1 | 0 | 10 | 8.267 |
| D18 | Flap open/Horns advanced | 0.1 | 0 | 10 | 8.733 |
| D9 | Flap closed/Horns advanced | 0.2 | 0 | 5 | 8.967 |
| D15 | Flap open/Horns advanced | 0.2 | 0 | 5 | 9 |
| D4 | Flap closed/Horns Normal | 0.1 | 0 | 5 | 9.1 |
| D22* | Flap open/Horns normal | 0.1 | 0 | 5 | 9.633 |
| D10* | Flap closed/Horns advanced | 0.1 | 0 | 5 | 9.667 |
| D16* | Flap open/Horns advanced | 0.1 | 0 | 5 | 9.667 |
| D21* | Flap open/Horns normal | 0.2 | 0 | 5 | 9.8 |
| N1** | Flap closed/Horns Normal | 0 | 0 | 0 | 9.833 |
| D1* | Flap closed/Horns Normal | 0.2 | 0 | 0 | 9.933 |
| N4* | Flap open/Horns Advanced | 0 | 0 | 0 | 9.933 |
| D2* | Flap closed/Horns Normal | 0.1 | 0 | 0 | 10.133 |
| D20*** | Flap open/Horns normal | 0.1 | 0 | 0 | 10.7 |
| D13*** | Flap open/Horns advanced | 0.2 | 0 | 0 | 10.733 |
| D14*** | Flap open/Horns advanced | 0.1 | 0 | 0 | 10.733 |
| D19*** | Flap open/Horns normal | 0.2 | 0 | 0 | 10.9 |
| N3*** | Flap closed/Horns Advanced | 0 | 0 | 0 | 10.9 |
| D8*** | Flap closed/Horns advanced | 0.1 | 0 | 0 | 11.133 |
| N2*** | Flap open/Horns Normal | 0 | 0 | 0 | 11.333 |
| D7*** | Flap closed/Horns advanced | 0.2 | 0 | 0 | 11.633 |

**denotes normal production,
*denotes not significantly different than normal production;
***denotes significantly higher values than normal production.
LSD = 0.59.

TABLE 37

Effect on IMOR with blender modifications, the addition of Wetting composition and desnity on Plant C.

| Treatment | Blender | Wetting Composition (%) | Resin Reduction (%) | Density reduction (%) | IB (mPa) |
|---|---|---|---|---|---|
| D17 | Flap open/Horns advanced | 0.2 | 0 | 10 | 0.14 |
| D5 | Flap closed/Horns Normal | 0.2 | 0 | 10 | 0.23 |
| D12 | Flap closed/Horns advanced | 0.1 | 0 | 10 | 0.243 |
| D3 | Flap closed/Horns Normal | 0.2 | 0 | 5 | 0.27 |
| D23 | Flap open/Horns normal | 0.2 | 0 | 10 | 0.303 |
| D15 | Flap open/Horns advanced | 0.2 | 0 | 5 | 0.32 |
| D6 | Flap closed/Horns Normal | 0.1 | 0 | 10 | 0.323 |
| D18* | Flap open/Horns advanced | 0.1 | 0 | 10 | 0.327 |
| D11* | Flap closed/Horns advanced | 0.2 | 0 | 10 | 0.333 |
| D24* | Flap open/Horns normal | 0.1 | 0 | 10 | 0.34 |
| D10* | Flap closed/Horns advanced | 0.1 | 0 | 5 | 0.363 |
| D21* | Flap open/Horns normal | 0.2 | 0 | 5 | 0.367 |
| D22* | Flap open/Horns normal | 0.1 | 0 | 5 | 0.377 |
| N4* | Flap open/Horns Advanced | 0 | 0 | 0 | 0.383 |
| D19* | Flap open/Horns normal | 0.2 | 0 | 0 | 0.403 |
| D4* | Flap closed/Horns Normal | 0.1 | 0 | 5 | 0.407 |
| D16* | Flap open/Horns advanced | 0.1 | 0 | 5 | 0.41 |
| D20* | Flap open/Horns normal | 0.1 | 0 | 0 | 0.413 |
| N1** | Flap closed/Horns Normal | 0 | 0 | 0 | 0.417 |
| D9* | Flap closed/Horns advanced | 0.2 | 0 | 5 | 0.42 |
| D1* | Flap closed/Horns Normal | 0.2 | 0 | 0 | 0.427 |
| D2* | Flap closed/Horns Normal | 0.1 | 0 | 0 | 0.43 |
| D7* | Flap closed/Horns advanced | 0.2 | 0 | 0 | 0.44 |
| D13* | Flap open/Horns advanced | 0.2 | 0 | 0 | 0.477 |
| N3* | Flap closed/Horns Advanced | 0 | 0 | 0 | 0.477 |
| N2* | Flap open/Horns Normal | 0 | 0 | 0 | 0.497 |
| D14* | Flap open/Horns advanced | 0.1 | 0 | 0 | 0.507 |
| D8*** | Flap closed/Horns advanced | 0.1 | 0 | 0 | 0.55 |

**denotes normal production,
*denotes not significantly different than normal production;
***denotes significantly higher values than normal production.
LSD = 0.07.

TABLE 38 treatments for Plant C achieve density savings as well as acceptable IB and MOR values:

| Treatment | Horn position | Flap position | Wetting composition (%) | Density Reduction (%) |
|---|---|---|---|---|
| D10 | Advanced | Closed | 0.1 | 5 |
| D16 | Advanced | Open | 0.1 | 5 |
| D21 | Normal | Open | 0.2 | 5 |
| D22 | Normal | Open | 0.1 | 5 |

TABLE 39

A summary of identical results from all trials and from all plants.

| Plant | Treatment | Horn position | Flap position | Wetting composition (%) | Resin Reduction (%) |
|---|---|---|---|---|---|
| A | R12 | Advanced | Closed | 0.10 | 10 |
| B | R30 | Advanced | Closed | 0.10 | 10 |
| C | R12 | Advanced | Closed | 0.10 | 10 |
| A | R10 | Advanced | Closed | 0.10 | 5 |
| B | R14 | Advanced | Closed | 0.10 | 5 |
| C | R10 | Advanced | Closed | 0.10 | 5 |
| A | R6 | Normal | Closed | 0.10 | 10 |
| B | R29 | Normal | Closed | 0.10 | 10 |
| C | R6 | Normal | Closed | 0.10 | 10 |
| A | R5 | Normal | Closed | 0.20 | 10 |
| B | R5 | Normal | Closed | 0.20 | 10 |
| C | R5 | Normal | Closed | 0.20 | 10 |
| A | R4 | Normal | Closed | 0.10 | 5 |
| B | R13 | Normal | Closed | 0.10 | 5 |
| C | R4 | Normal | Closed | 0.10 | 5 |

Example 2D

The Effect of Different Surfactants on Contact Angle

Table 40 below shows the sessile advancing contact angles of distilled water on oven dry *P. radiata* containing various surfactants.

The contact angle data is recorded using water because resins, by their nature, can continue to polymerise resulting in changes in viscosity which will change the wetting behaviour of the resin/surfactant mix. Thus the only reliable comparison is to determine the relative effects of the surfactants in water, the viscosity of which effectively does not change with either age, or changes in temperature (around room temperature). Water is also present in all amino resins as the carrier of the resin solids so it is important to understand the effect of the surfactant on water because this will have a direct relationship on the wetting performance of the resin.

The contact angle shown below is the average of at least 5 measurements. The measurements were taken after 1 second and in some instances after half a second. Where the entry is "n/a" it indicates complete wetting i.e. a contact angle of 0° or very close to 0°.

TABLE 40 comparison of contact angle measurements with water on over dry *P. radiata*

| Surfactant (%) | Octanol (%) | Contact angle @ 1 sec | Contact angle @ 0.5 sec |
|---|---|---|---|
| Nil | 0 | 71.83 | |
| Teric N9 @ 0.025 | 0.04 | 20.2 | |
| Pulse @ 0.1 | 0.1 | 10.11 | |
| SDS @ 0.05 | 0.1 | 31.0 | |
| SDS @ 0.1 | 0.1 | 9.5 | |
| SDS @ 0.1 | 0.25 | 8.99 | |
| Dynol @ 0.1 | 0.1 | 11.74 | |
| Surfynol @ 0.1 | 0.1 | 35.2 | |
| Tween @ 0.1 | 0.1 | 26.31 | |
| DS10025 @ 0.1 | 0.1 | n/a | 9.08 |
| DS10025 @ 0.1 | 0.3 | n/a | 7.91 |
| DS10025 @ 0.3 | 0.3 | 6.92 | 13.32 |
| DS10030 @ 0.1 | 0.1 | 14.73 | 22.38 |
| DS10030 @ 0.1 | 0.3 | 16.52 | 16.94 |
| DS10030 @ 0.3 | 0.3 | 4.57 | 7.27 |
| Teric 13A9 @ 0.1 | 0.1 | 7.77 | 13.10 |
| Teric 13A9 @ 0.1 | 0.3 | n/a | 9.96 |
| Teric 13A9 @ 0.3 | 0.3 | 3.97 | 4.89** |
| Teric BL8 @ 0.1 | 0.1 | n/a | 7.18 |
| Teric BL8 @ 0.1 | 0.3 | 9.07 | 10.35 |
| Teric BL8 @ 0.3 | 0.3 | n/a | n/a |

In the absence of the wetting composition, the water contact angle of the substrate surface is 71.83. It can be seen that upon addition of the wetting composition according to various embodiments of the invention, the contact angle is significantly decreased.

Example 3

Wettability of an Agricultural Composition Before and after Addition of the Welling Composition Table 41 shows fourteen agricultural compositions and one control. The samples were labelled Treatment Nos 1 to 15. Each agricultural composition (except No. 13) comprises an active. For example, Roundup® (a herbicide sold by Monsanto) comprises glyphosate as an active ingredient. Roundup also includes a surfactant. The agricultural composition referred to Credit® is glyphosate in the absence of a surfactant.

Prior to use, some of the agricultural compositions were mixed with the wetting composition prepared in Example 1 (Nos 7 to 12 and 14). The wetting composition was added to the agricultural composition and the mixture was stirred before use. The agricultural compositions were then separately applied to foliage using known techniques.

TABLE 41

Agricultural compositions

| TRT No. | Agricultural composition | Active | Surfactant g/l of spray |
|---|---|---|---|
| 1 | Untreated | 0 | 0 |
| 2 | Roundup 360 @ 4.0 l/Ha | 360 gai/l | unknown |
| 3 | Roundup CT @ 3.2 l/ha | 450 gai/l | 2.105 g/l |
| 4 | Credit @ 2.67 l/ha | 540 gai/l | 0 |
| 5 | Credit @ 1.87 l/ha | 540 gai/l | 0 |

TABLE 41-continued

Agricultural compositions

| TRT No. | Agricultural composition | Active | Surfactant g/l of spray |
|---|---|---|---|
| 6 | Credit @ 1.335 l/ha | 540 gai/l | 0 |
| 7 | Credit @ 2.67 l/ha + wetting composition @ 0.5 wt % | 540 gai/l | 5 g/l |
| 8 | Credit @ 1.87 l/ha + wetting composition @ 0.5 wt % | 540 gai/l | 5 g/l |
| 9 | Credit @ 1.335 l/ha + wetting composition @ 0.5 wt % | 540 gai/l | 5 g/l |
| 10 | Credit @ 1.87 l/ha + wetting composition @ 0.125 wt % | 540 gai/l | 1.25 g/l |
| 11 | Credit @ 1.87 l/ha + wetting composition @ 0.25 wt % | 540 gai/l | 2.5 g/l |
| 12 | Credit @ 1.87 l/ha + wetting composition @ 1.0 wt % | 540 gai/l | 10 g/l |
| 13 | wetting composition @ 1.0 wt % | 0 | 10 g/l |
| 14 | Roundup @ 2.0 l/ha + wetting composition @ 0.25 wt % | 360 gai/l | u/k + 2.5 g/l |
| 15 | Roundup @ 2.0 l/ha | 360 gai/l | unknown |

"gai" grams of active ingredient
Roundup CT = 125 gram of surfactant/lt of Roundup CT Upon addition of the wetting composition to the agricultural composition, it was found that the wetting composition was at least as effective as Pulse®. Pulse® is a surfactant that was, but is no longer added to Roundup. The active ingredient of Pulse is polydimethylsiloxane (PDMS).

Example 4

Impregnation of Décor Paper with Resin Before and after Addition of the Wetting Composition In the Absence of the Wetting Composition Décor paper was impregnated with a urea formaldehyde (UF) resin by passing the paper under tension over a pre-wetting roller. A film of resin was picked up by the roller and transferred to the bottom side of the paper. The paper was then completely immersed in a resin bath of UF to wet the top-side of the paper.

The saturated and dried UF resin impregnated paper was coated with a melamine formaldehyde (MF) resin using gravure rollers.

In the Presence of the Wetting Composition

The method described immediately above was repeated. However, prior to immersing the paper in the UF resin bath 0.5 wt % of the wetting composition prepared in Example 1 was stirred into the bath. The result was a 10% reduction in the use of MF resin.

Many modifications will be apparent to those skilled in the art without departing from the scope of the present invention.

The claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The invention claimed is:

1. A method for wetting a low energy surface with an aqueous liquid, the method comprising the steps of:
    adding a wetting composition to the aqueous liquid to lower the surface tension of the liquid and thereby increase the ability of the aqueous liquid to wet the low energy surface; and
    contacting the low energy surface with the liquid comprising the wetting composition;
    wherein the wetting composition comprises:
        from about 50 wt % to 70 wt % of a C5 to C12 alcohol; and
        greater than or equal to about 30 wt % of a surfactant capable of forming micelles, the surfactant being selected from one or more anionic, cationic, and non-ionic surfactants;
    wherein the C5 to C12 alcohol and the surfactant together make up 90 wt % or more of the wetting composition; and
    wherein the amount of wetting composition added to the aqueous liquid is from about 0.1 to 5 vol %.

2. The method of claim 1, wherein the low energy surface is the surface of a natural product.

3. The method of claim 2, wherein the natural product comprises natural fibres, a wood or timber-based product, leather, a seed or plant foliage.

4. The method of claim 1, wherein the low energy surface is artificial or chemically modified.

5. The method of claim 1 wherein the surfactant comprises one or more components selected from the group consisting of:
    alcohol alkoxylates, sulfonates, or phosphates;
    ethylene oxide/propylene oxide (EO/PO) blocked polymers;
    C6C12 saturated or monounsaturated alkyl amine oxides;
    mono- or di-sulfonated aliphatic alcohols, or their corresponding sulfonic acids;
    alpha-olefin sulfonates or sulfonic acids;
    alkane sulfonates or sulfonic acids;
    alkoxyalkyl sulfonates or phosphates;
    linear alkyl benzene sulfonate (LABS); and
    sodium or ammonium salts of dioctyl sulpho succinate.

6. The method of claim 1, wherein the surfactant is an alcohol alkoxylate.

7. The method of claim 1, wherein the C5 to C12 alcohol is octanol.

8. The method of claim 1, wherein the composition further comprises one or more additives selected from a defoamer, an active compound, a salt, a dye, solid particles, and a fragrance.

9. The method according to claim 8, wherein the composition comprises a fragrance selected from vanillin and isovanillin.

10. The method of claim 1, wherein the aqueous liquid is water.

11. The method of claim 1, wherein the aqueous liquid is an aqueous-based resin.

12. The method of claim 1, wherein the aqueous liquid comprises an agricultural composition.

13. The method of claim 1, wherein the aqueous liquid comprises a drug.

14. The method according to claim 1, wherein the aqueous liquid comprising the wetting composition is in the form of an aerosol comprising the aqueous liquid composition.

15. The method of claim 14, wherein the aerosol is a spray paint, a cosmetic, an agricultural spray or a cleaning agent.

16. The method of claim 1, wherein the wetting composition comprises greater than or equal to about 50 wt % of a C7 to C12 alcohol.

17. A method for wetting a low energy surface with an aqueous liquid, wherein the low energy surface comprises a wood or timber-based product, a seed, or plant foliage, the method comprising the steps of:
    adding a wetting composition to the aqueous liquid to lower the surface tension of the liquid and thereby increase the ability of the aqueous liquid to wet the low energy surface; and
    contacting the low energy surface with the liquid comprising the wetting composition;
    wherein the wetting composition comprises:
        from about 50 wt % to 70 wt % of a C5 to C12 alcohol;
        greater than or equal to about 30 wt % of a surfactant capable of forming micelles, wherein the surfactant is an alcohol alkoxylate,
    wherein the C5 to C12 alcohol and the surfactant together make up 90 wt % or more of the wetting composition; and
    wherein the amount of wetting composition added to the aqueous liquid is from about 0.1 to 5 vol %.

* * * * *